United States Patent
Kauffman et al.

(10) Patent No.: US 11,150,171 B2
(45) Date of Patent: Oct. 19, 2021

(54) MEASURING PROPERTIES OF FLOUR, DOUGH, AND OTHER SOLIDS

(71) Applicant: PerkinElmer Health Sciences, Inc., Waltham, MA (US)

(72) Inventors: Charles Kauffman, Peoria, IL (US); Ashley Combs, Mount Pulaski, IL (US); Jennifer S. Robinson, Plymouth, MN (US); Darrel Nelson, Winona, MN (US); Ivan Alberto Alden, Marsfield (AU); Jennifer Minh Chau Dang, Eastwood (AU)

(73) Assignees: PerkinElmer Health Sciences, Inc., Waltham, MA (US); Bay State Milling Company, Minneapolis, MN (US); Perten Instruments of Australia, Pty Ltd., Macquarie Park (AU)

( * ) Notice: Subject to any disclaimer, the term of this patent is extended or adjusted under 35 U.S.C. 154(b) by 287 days.

(21) Appl. No.: 16/368,017

(22) Filed: Mar. 28, 2019

(65) Prior Publication Data
US 2019/0301990 A1    Oct. 3, 2019

Related U.S. Application Data

(60) Provisional application No. 62/650,967, filed on Mar. 30, 2018.

(51) Int. Cl.
*G01N 11/14* (2006.01)
*G01N 33/10* (2006.01)
(Continued)

(52) U.S. Cl.
CPC ........ *G01N 11/14* (2013.01); *B01F 15/00123* (2013.01); *G01N 33/10* (2013.01);
(Continued)

(58) Field of Classification Search
CPC . G01N 11/14; G01N 33/10; G01N 2011/0006
See application file for complete search history.

(56) References Cited

U.S. PATENT DOCUMENTS

| 5,509,297 A | 4/1996 | Miiller et al. |
| 2013/0118235 A1 | 5/2013 | Morgan et al. |

FOREIGN PATENT DOCUMENTS

EP    0428241 A1    5/1991

OTHER PUBLICATIONS

Jul. 18, 2019—(WO) International Search Report and Written Opinion Appl PCT/US2019/024786.
(Continued)

*Primary Examiner* — Walter L Lindsay, Jr.
*Assistant Examiner* — Andrew V Do
(74) *Attorney, Agent, or Firm* — Banner & Witcoff, Ltd.

(57) ABSTRACT

Described herein are systems and methods for the automated adjustment of flour property measurement equipment such as dough rheometers. The systems and methods allow measurements of flour and dough to be performed on different rheometers with consistent results, regardless of the manufacturer or location of the rheometers. The systems and methods described herein allow a second rheometer, for example, that is deployed in the field to provide results that are consistent with a first dough rheometer, for example, that may be at a different location, or the same location but of the same or different manufacturer. The systems and methods can be used to calibrate, remotely and in real-time, dough rheometers that are deployed in various locations.

19 Claims, 10 Drawing Sheets

(51) Int. Cl.
   *B01F 15/00*  (2006.01)
   *G01N 11/00*  (2006.01)
   *B29B 7/28*   (2006.01)
   *A21C 1/00*   (2006.01)

(52) U.S. Cl.
   CPC ............... *A21C 1/00* (2013.01); *B29B 7/286* (2013.01); *G01N 2011/0006* (2013.01); *G01N 2011/0026* (2013.01); *G01N 2011/0046* (2013.01)

(56) References Cited

OTHER PUBLICATIONS

Luz Altuma, et al "Torque Measurement in Real Time during Mixing and Kneading of Bread Dough with High Content of Resistant Maize Starch and Enzymes", International Journal of Food Engineering, vol. 12, No. 8, Jan. 1, 2016, pp. 1-10.
Beaupre D, et al., "Comparison of Concrete Rheometers: International Tests at MB (Cleveland, OH, USA) in May 2003".

MEASURING PROPERTIES OF FLOUR, DOUGH, AND OTHER SOLIDS

This application claims priority to and the benefit of U.S. Provisional Patent Application No. 62/650,097, filed Mar. 30, 2018, the above-identified application is incorporated by reference herein in its entirety.

TECHNICAL FIELD

This invention relates generally to methods, systems, and architectures for measuring properties of flour, dough, and other solids. In particular embodiments, the invention relates to the automated calibrating of rheometers for measuring properties of flour.

BACKGROUND

The ability to measure rheological properties of flour and dough is important in the food industry for ensuring product quality and consistency. It is important for millers and commercial bakers to measure properties of flour to obtain a consistent final product (e.g., a bread, cake, or the like with a consistent texture). For example, it is useful to measure how much water a particular type of flour absorbs relative to another type of flour and how well the resulting dough withstands mechanical stress (e.g., shear) during mixing. A commercial baker uses the information from these measurements to optimize the amount of water that is added to the flour on a case-by-case basis to minimize flour consumption (e.g., to decrease the amount of flour that is wasted) and to ensure consistent product quality.

These measurements can be performed, for example, using flour analysis equipment, e.g., dough rheometers such as the doughLAB marketed under the PERTEN brand. A dough rheometer includes a container for holding flour with water, one or more mixing blades for mixing the flour and water to form dough, and one or more sensors for measuring the torque encountered by the mixing blade as the dough is mixed.

Industry-standard tests are used to determine relative water absorption (i.e., the amount of water required to achieve a pre-determined consistency) by the flour and how dough made with the flour responds to mechanical stress. In one such test, an experimenter adds 300 grams of 14% moisture flour (with the weight adjusted for the actual moisture content of the flour) to the mixing container of a dough rheometer. Water is then added until dough is obtained with a specific rheological property, i.e., a measured torque of 500 Force Units (1 Force Unit=9.806 mNm). The amount of water that is added to create a dough with this target property is expressed as a percentage of the original flour weight, and is termed the Water Absorption. For example, if 150 grams of water are added to yield a 500 Force Unit dough, the flour is said to have a 50% water absorption (e.g., 150 grams of water/300 grams of flour=50%).

To determine how well the dough withstands mechanical stress, the dough is mixed in the dough rheometer at a specified speed while the torque encountered by the mixing blade(s) is measured for a certain period of time. For each test, three "torque curves" (i.e., time-varying torque spectra) can be generated/derived from the raw data that represents the measured torque values as a function of time, where the raw data is typically obtained by taking measurements every 0.01 seconds. The raw data is typically filtered or down-sampled (e.g., at a rate of one sample per second), and from the down-sampled data, three corresponding torque curves/spectra are generated or derived reflecting a "minimum", "maximum", and "average" torque value as a function of time (e.g., for a down-sample rate of 1 sample per second, each the maximum, minimum, and average torque value within the one-second down-sample window is computed and attributed to the respective curves/spectra). The difference between the minimum and maximum torque curves for a given experiment and corresponding instrument can be referred to as the torque "bandwidth". The derived torque curve, comprising minimum, maximum, and average curves, generally includes a peak (e.g., maximum) torque, although it can be understood that the peak of the "average" curve is the peak that is typically used for rheological computations. The torque typically decreases after this peak is reached. The time at which this peak torque occurs can be used as another metric for characterizing the flour.

When dough made from the same flour is measured with different rheological analysis equipment (e.g., deployed in various mills), the results obtained rarely provide the same values. The continuous wear on the blades and the bowl of the equipment and the inherent variability of the large sample interfaces used during tests are some causes of the discrepancies between measurements performed with different devices. Moreover, discrepancies exist between results from instruments using the same testing principles but produced by different manufacturers.

These discrepant results for the same flour create problems for millers and bakers. Food manufacturers may, for example, inappropriately reject flour because of the discrepant results obtained from uncalibrated rheological measurement equipment. For example, a miller in the midwest of the United States may ship a flour order to a food manufacturer in the northeast United States, having confirmed the flour was within specifications at the mill. Upon receipt, the food manufacturer may obtain a discrepant measurement from their instrument (e.g., due to a dent in the mixing bowl or wear on the mixing blade). Because food manufacturers generally have strict requirements for product consistency, the entire shipment of flour may be unnecessarily rejected. The miller will then bear the costs of transporting the flour to another manufacturer or back to the mill, and the food manufacturer will bear the cost of lost manufacturing time and wasted analysis time. In the event of a disputed measurement, one or both parties can send a sample of the flour to a third-party industry contract laboratory as arbiter, where the sample is measured by a rheometer understood to meet industry standards.

There is currently no standard, traceable material (e.g., a flour-like material) to which dough rheometers can be calibrated, because of the inconsistent rheological and material properties of different flour types and between different flour batches. Furthermore, these flour properties, such as water content and water absorption capacity, may vary over time. While the torque sensor of a dough rheometer can be calibrated using a certified weight, a dough rheometer, as a whole, cannot be calibrated to a fixed standard. Since each individual rheometer often provides different results for the same sample, it is difficult or impossible to compare results obtained from different devices.

There is thus a need for improved systems and methods for calibrating flour analysis equipment such as dough rheometers.

SUMMARY

Described herein are systems and methods for the automated calibration of flour property measurement equipment (e.g., dough rheometers). The systems and methods allow measurements of flour and dough to be performed on different rheometers with consistent results, regardless of the manufacturer or location of the rheometers. The systems and methods described herein allow a second rheometer, for example, that is deployed in the field (e.g., at a flour mill or a food manufacturer) to provide results that are consistent with a first dough rheometer, for example, that may be at a different location, or the same location but of the same or different manufacturer. The systems and methods herein are not limited to first and second rheometers, but allow for calibration of, for example, a third rheometer to the second rheometer, wherein it is understood that the "first" rheometer can be a set of one or more rheometers that are affiliated in some manner (e.g., same model, same manufacturer, same size, and/or same location, etc.), and similarly the second rheometer and third rheometer can each be a set of one or more rheometers that are affiliated in some manner. It can thus be understood that the disclosed systems and methods can be used to calibrate, remotely and/or in real-time, dough rheometers that are deployed in various locations (e.g., flour mills, e.g., food manufacturing locations, e.g., laboratories). As will be provided herein, the result of the disclosed methods and systems is a time-dependent and flour-dependent adjustment model that characterizes the differences between torque curve data measured at different rheometers.

The disclosed methods and systems include a system for generating a calibrated measurement of one or more properties of a sample mixture, the sample mixture comprising (i) flour of a known flour type at known moisture; and (ii) a controlled amount of liquid adjusted to the known moisture of the sample, the system comprising: at least one first and at least one second measuring device, each measuring device further comprising a mixing container; at least one mixing blade; at least one torque sensor for generating a time-varying measurement of sample torque encountered by one or more of the at least one mixing blade when mixing the sample mixture in the mixing container; a processor; and, a memory having instructions stored thereon, wherein the instructions, when executed by the processor, cause the processor to: (i) adjust the generated time-varying measurement of sample torque of the at least one second measuring device, the adjustment based on a comparison of: (a) at least one time-varying measurement of sample torque determined by the at least one first measuring device operating, respectively, on a first portion of a calibration sample comprising the known flour type and a calibration amount of the liquid, and (b) at least one time-varying measurement of sample torque determined by the respective second measuring device operating on a second portion of the calibration sample and an amount of the liquid that is based on the calibration amount of the liquid; and, (ii) determine the one or more properties of the sample mixture based on the adjusted time-varying measurement of sample torque. The instructions, when executed by the processor, cause the processor to adjust the generated time-varying measurement of sample torque of the at least one second measuring device using an adjustment model based on the comparison of (a) and (b). The sample mixture comprises flour of the same type as the calibration sample, but from a different batch than the calibration sample. The system is a dough rheometer, and the one or more properties of the sample mixture include rheological properties that include at least one of water absorption and mixing characteristics. The at least one time-varying measurement of sample torque comprises three derived torque curves, where the three derived curves include down-sampled or filtered, time-varying data derived from the at least one torque sensor that measures the time-varying sample torque, the down-sampled time-varying representations including a minimum time-varying torque spectrum, a maximum time-varying torque spectrum, and an average time-varying torque spectrum.

The processor instructions to adjust the generated time-varying measurement of sample torque of the at least one second measuring device, include processor instructions to generate an adjustment model by comparing (i) at least one of the derived minimum, maximum, and average down-sampled time-varying spectra of sample torque determined by the at least one first measuring device operating, respectively, on a first portion of a calibration sample comprising the known flour type and a calibration amount of the liquid, with (ii) at least one of the derived minimum, maximum, and average down-sampled time-varying spectra of sample torque determined by the at least one second measuring device operating, respectively, on the second portion of the calibration sample comprising the known flour type and the calibration amount of the liquid. The adjustment model further comprises instructions to adjust one or more of the derived minimum, maximum, and average down-sampled time-varying spectra associated with the second measuring device with data from each of the minimum, maximum, and average down-sampled time-varying spectra of sample torque associated with the first measuring device. The at least one time-varying measurement of sample torque determined by the at least one first measuring device operating, respectively, on a first portion of a calibration sample comprising the known flour type and a calibration amount of the liquid, comprises; at least two different measurements of torque determined by each of the at least one first measuring device operating on the calibration sample, wherein the at least two different measurements are combined. The at least two different measurements from each first measurement device are combined by averaging in some embodiments. The at least two different measurements from each first measurement device are combined to provide a combined result from each first measurement device, and the combined result from each first measurement device is further combined to generate a composite result from all of first measurement devices.

Each measuring device further comprises at least one temperature sensor for controlling the thermal input to the sample, and at least one speed sensor for providing a measurement of the blades or other mixing implements.

In embodiments, the comparison is based on at least one of: a regression, a multivariate regression, a linear regression, a multiple linear regression, a multivariate linear regression, a curve fitting, a Honigs' regression, a linear least squares, a Gaussian, and a nearest neighbor determination.

Also disclosed is a system for generating a calibrated measurement of one or more properties of a sample mixture comprising (i) flour of a known flour type and moisture, and known quantity and (ii) a determined amount of a liquid adjusted to the known moisture of the sample, the system comprising: a mixing container; one or more mixing blades; one or more torque sensors for generating a time-varying measurement of sample torque encountered by one or more of the one or more mixing blades when mixing the sample mixture in the mixing container; a processor; and, a memory having instructions stored thereon, wherein the instructions, when executed by the processor, cause the processor to: (i) adjust, in real-time, the time-varying measurement of sample torque using torque curve data generated from a set of first calibration rheometers operating, respectively, on one or more calibration samples comprising the known flour type; and (ii) determine the one or more properties of the sample mixture from the adjusted time-varying measurement of sample torque. The instructions, when executed by the processor, cause the processor to adjust the generated time-varying measurement of sample torque using an adjustment model, wherein the adjustment model is based on a comparison of: (a) torque curve data generated from the set of first calibration rheometers, each first calibration rheometer operating on (i) at least one first portion of a calibration sample comprising the known flour type at known moisture and (ii) a calibration amount of the liquid, adjusted to the known moisture of the sample; and (b) torque curve data generated by the dough rheometer operating on a second portion of the calibration sample and an amount of the liquid that is based on the calibration amounts of liquid used in the set of first calibration rheometers. The torque curve data generated from the set of second calibration rheometers reflects a calibration using one or more torque curves generated from a set of first calibration rheometers for samples comprising the known flour type. The instructions, when executed by the processor, cause the processor to adjust the time-varying measurement of sample torque to the torque curve data using an adjustment model specific to the known flour type at known moisture. Each of the one or more calibration samples operated on by the set of first calibration rheometers comprises a calibration amount of the liquid, adjusted to known moisture of the sample.

Also disclosed is a system for generating a torque curve adjustment model applicable for a dough mixture comprising a known flour type at known moisture, the system comprising: a mixing container; one or more mixing blades; one or more torque sensors for generating a time-varying measurement of sample torque encountered by one or more of the one or more mixing blades when mixing a calibration sample mixture comprising: (i) a first portion of a calibration sample of flour of the known flour type and moisture, and known quantity and (ii) a determined calibration amount of a liquid, adjusted to the known moisture of the sample, in the mixing container; a processor; and a memory having instructions stored thereon, wherein the instructions, when executed by the processor, cause the processor to: (a) generate a time-varying measurement of torque for the calibration sample mixture; and (b) determine the adjustment model applicable for a non-calibration rheometer and the known flour type at known moisture using at least (i) the time-varying measurement of torque for the calibration sample mixture and (ii) a torque data stream generated by the non-calibration rheometer for a mixture comprising (x) a second portion of the calibration sample of flour of the known flour type and moisture and (y) an amount of the liquid based on the calibration amount of the liquid, adjusted to the known moisture of the sample. The adjustment model is determined using a plurality of torque data streams generated using the set of first calibrating rheometers, and wherein each of the mixtures of the known flour type and moisture for the set of first calibration rheometers comprises a calibration amount of the liquid. In an embodiment, the system is a member of a set of first calibration rheometers, wherein the time-varying measurement of torque for the calibration sample mixture is, itself, corrected using an adjustment model determined for the member of the set of first calibration rheometers using one or more torque data streams generated by one or more members of a set of reference calibration rheometers.

In certain embodiments, multiple flour samples from the same batch/lot of a given type of flour are tested by multiple calibration machines to create comparison data, e.g., a torque adjustment model, for that flour type. It has been found that an effective torque adjustment model for a given flour type can be generated for a given ("second") rheometer, for example, a dough rheometer deployed in the field (e.g., at a flour mill or food manufacturing location) using multiple 'master' ("first") rheometers as reference rheometers. Experiments are performed by both (i) the field rheometer being calibrated and (ii) each of the 'master' rheometers on samples taken from the same batch/lot of flour of a particular flour type, said flour preferably having aged sufficiently at the time of the experiments such that its properties are relatively stable (e.g., said flour having been milled at least a week prior to its use in the experiments), Furthermore, it is preferable that calibration flour samples are tested on all rheometers with minimal delay (e.g., within a period of 48-96 hours or less) to further reduce variability caused by time-changing flour properties. Torque data (e.g., the minimum, maximum and average torque values over time) generated from the field rheometer is analyzed together (e.g., compared) with the corresponding torque data provided by the 'master' rheometers (e.g., using chemometrics software performing multivariate analysis or multiple linear regression on each of the minimum, maximum and average torque spectra) tested under substantially identical conditions, to create an adjustment model that will be applied to future torque curve data measurements at the field rheometer, for that flour type. The adjustment model generated for the field rheometer, applicable for that flour type and for that rheometer, can then be implemented in the field rheometer to automatically and reliably adjust, in real-time, subsequent measurements generated by said field rheometer for samples taken from other batches of that flour type and measured by the same master rheometer(s). In this way, a torque adjustment model can be determined for each of multiple flour types for a given field ("second") rheometer in relation to a given master rheometer. The adjustment models can be automatically implemented to adjust torque measurements generated by the field rheometer on samples of the same flour type obtained from other batches, thereby providing consistency between field and 'master' measurements. Similarly, adjustment models can be determined for each of a plurality of field (or "second") rheometers, then implemented such that measurements of a given flour sample by each of the plurality of field rheometers are in agreement with the 'master' (or "first") rheometers and in agreement with each other. This solves the problem posed by machine-to-machine variability, within and between brands, for these kinds of measurements, thereby enhancing comparability and reproducibility of results, allowing more accurate determination that samples meet a given property specification, and avoiding the waste and expense caused by inaccurate measurements.

Moreover, in certain embodiments, additional benefit is achieved by using multiple tiers or sets of rheometers. For example, an adjustment model for a particular flour type may be determined from two or more sets or tiers of machines, where a second tier of multiple rheometers are, themselves, calibrated to a first tier of rheometers, and a third tier of rheometers may in-turn be calibrated with the second tier/set (and hence the first tier/set). In certain embodiments, the second tier (which produces adjustment models to calibrate to the first tier rheometers) has more machines (greater redundancy) than the first tier.

The systems and methods presented herein provide for calibration of a dough rheometer in a comprehensive and systematic manner. Workflows and computational routines are presented that provide more accurate calibration of a dough rheometer. Furthermore, in some implementations, torque adjustment models for each of a set of rheometers are determined for each of a set of flour types, and may be updated every so often (e.g., weekly, monthly, quarterly, biannually, or annually) using the methods and systems described herein.

In one aspect, the present disclosure is directed to a system (e.g., a dough rheometer) for generating a calibrated measurement of one or more properties (e.g., rheological properties, water absorption and/or mixing characteristics) of a sample mixture, the sample mixture comprising (i) flour of a known flour type and moisture; and (ii) a controlled (e.g., to achieve a certain torque value, or a predetermined) amount of liquid (e.g., water), adjusted to the known moisture of the sample, the system comprising: at least one first and at least one second measuring device, each measuring device comprising: a mixing container (e.g., a stainless steel bowl, or other enclosure); one or more mixing blades (e.g., a sigmoid z-arm mixing blade); one or more temperature sensors for controlling thermal input; one or more speed sensors to control mechanical input; and one or more torque sensors for generating a time-varying (e.g., continuous) measurement of sample torque encountered by one or more of the one or more of the one or more mixing blades when mixing the sample mixture in the mixing container; a processor; and a memory (e.g., external to or embedded in the processor) having instructions stored thereon, wherein the instructions, when executed by the processor, cause the processor to: adjust (e.g., in real-time, during data acquisition) the generated time-varying measurement of sample torque of the at least one second measuring device, the adjustment based on a comparison of: (i) at least one time-varying measurement of sample torque (e.g., a combined average torque data stream, e.g., combined minimum, maximum and average torque curves) determined by the at least one first measuring device (e.g., one or more torque sensors associated with at least one first measuring device, e.g., a set of one or more, e.g., one, two, three, or more, master dough rheometers) operating, respectively, on a first portion of a calibration sample comprising the known flour type at known moisture, and a calibration amount (e.g., to achieve a certain torque value) of the liquid, adjusted for the known moisture of the sample, and, (ii) at least one time-varying measurement of sample torque determined by the respective second measuring device operating on a second portion of the calibration sample and an amount of the liquid that is based on the calibration amount (e.g., the exact same amount; e.g., an amount that can be combined with other first amounts from the same or other first measuring device(s), e.g., to generate an average amount, e.g., to generate a median amount, e.g., to generate a statistically relevant amount); and determine (e.g., and display a representation of) the one or more properties (e.g., an adjusted torque curve, a calibrated rheological property value, and/or an indication of compliance or non-compliance with a product specification) of the sample mixture based on the adjusted time-varying measurement of sample torque.

In certain embodiments, the instructions, when executed by the processor, cause the processor to adjust the generated time-varying measurement of sample torque of the at least one second measuring device using an adjustment model based on the comparison of (i) and (ii).

In certain embodiments, the sample mixture comprises flour of the same type as that of the calibration sample, but from a different batch than that of the calibration sample.

In another aspect, the disclosed methods and systems are directed to a system (e.g., a dough rheometer) for generating a calibrated, (e.g., field-based) measurement of one or more properties (e.g., rheological properties, e.g., water absorption and/or mixing characteristics) of a sample mixture comprising (i) flour of a known flour type and known quantity and (ii) a determined (e.g., to achieve a certain (e.g., peak) torque value) amount of a liquid (e.g., water), the system comprising: a mixing container (e.g., a stainless steel bowl, or other enclosure); one or more mixing blades (e.g., a sigmoid z-arm mixing blade); one or more temperature sensors to control thermal input; one or more speed sensors to control mechanical input; one or more torque sensors for generating a time-varying (e.g., continuous) measurement of sample torque encountered by one or more of the one or more mixing blades when mixing the sample mixture in the mixing container; a processor; and a memory (e.g., external to or embedded in the processor) having instructions stored thereon, wherein the instructions, when executed by the processor, cause the processor to: adjust (e.g., in real-time, during data acquisition) the time-varying measurement of sample torque (e.g., by application of an adjustment model) using torque curve data generated from a set of first calibration rheometers (e.g., a set of one or more, e.g., one, two, three, or more, master dough rheometers) operating, respectively, on one or more calibration samples comprising the known flour type [e.g., and a calibration amount of the liquid (e.g., to achieve the certain torque value)]; and determine (e.g., and display a representation of) the one or more properties (e.g., an adjusted torque curve, a calibrated rheological property value, and/or an indication of compliance or non-compliance with a product specification) of the sample mixture from the adjusted time-varying measurement of sample torque.

In certain embodiments, the system is a dough rheometer (e.g., a field dough rheometer), and the instructions, when executed by the processor, cause the processor to adjust the generated time-varying measurement of sample torque using an adjustment model, wherein the adjustment model is based on a comparison of: (i) torque curve data (comprising minimum, maximum, average curve data) generated from the set of first calibration rheometers, each first calibration rheometer operating on (a) a first portion of a calibration sample comprising the known flour type at a known moisture, and (b) a calibration amount of the liquid (e.g., an amount of liquid to achieve the certain peak torque value); and (ii) torque curve data (comprising minimum, maximum, and average curve data) generated by the dough rheometer operating on a second portion of the calibration sample and an amount of the liquid that is based on the calibration amounts of liquid used in the set of first calibration rheometers (e.g., the exact same amount, e.g., an average amount, e.g., a median amount, e.g., a statistically relevant amount). The first and second portions of the calibration sample are from the same batch, although subsequent sample mixtures to be tested may comprise flour from a different batch than that of the calibration sample.

In certain embodiments, the torque curve data (comprising a minimum, maximum, and average curve) generated from the set of first calibration rheometers reflects a calibration (e.g., has been previously calibrated) using torque curve data (comprising a minimum, maximum, and average curve) generated from one or more industry-accepted third-party reference laboratory dough rheometers.

In certain embodiments, the instructions, when executed by the processor, cause the processor to adjust the time-varying measurement of (e.g., field-based) sample torque to the torque curve data using an adjustment model specific to the known flour type (e.g., wherein said adjustment model is also device-specific, e.g., specific to the particular rheometer of the system). In certain embodiments, the adjustment model utilizes all three of the derived minimum, maximum and average torque curve data (e.g., from the master rheometer(s)) to adjust each of the measured (derived) minimum, maximum, and average torque sample curves (i.e., from the field rheometer), in real time. In other embodiments, less than all three of the (derived) minimum, maximum, and average torque curve data can be used to adjust each of the corresponding measured (derived) minimum, maximum, and average torque sample curves. More specifically, in such embodiments, for a point in time, t, the inputs (in addition to time) to a linear regression/adjustment model comprise or include (but are not necessarily limited to): three (3) data points from the torque curve data, T, from first set rheometers (i.e., one data point from each of the minimum, maximum, and average torque curve data at time t) and one (1) data point from time t from one of the derived minimum, maximum, or average torque curves from a second set rheometer. In such an embodiment, a point-by-point adjustment or alignment of each of the points on each of the derived minimum, maximum, or average torque curves from a second set rheometer can be adjusted/calibrated to the first set rheometer torque curve data, T, using data from all three of the first set rheometer curves, T. (As used herein, adjustment model and alignment model refer to the same item, which may be further implemented as an adjustment module or an alignment module.) In certain embodiments, each of the one or more calibration samples operated on by the set of first calibration rheometers comprises a calibration amount (e.g., to achieve a certain (e.g., peak) torque value) of the liquid (e.g., amounts each specific to corresponding members of the set of first rheometers).

In another aspect, the disclosed methods and systems are directed to a system (e.g., a calibration rheometer, e.g., a member of a set of first calibration rheometers) for generating a torque curve adjustment model applicable for a dough mixture comprising a known flour type, the system comprising: a mixing container (e.g., a stainless steel bowl, or other enclosure); one or more mixing blades (e.g., a sigmoid z-arm mixing blade); one or more torque sensors for generating a time-varying (e.g., continuous) measurement of sample torque encountered by one or more of the one or more mixing blades when mixing a calibration sample mixture comprising (i) a first portion of a calibration sample of flour of the known flour type and known quantity and (ii) a determined (e.g., to achieve a certain (e.g., peak) torque value) calibration amount of a liquid (e.g., water) in the mixing container; a processor; and a memory (e.g., external to or embedded in the processor) having instructions stored thereon, wherein the instructions, when executed by the processor, cause the processor to: generate a time-varying measurement of torque for the calibration sample mixture from which minimum, maximum, and average torque time-varying curves can be derived; and determine the adjustment model applicable for a non-calibration (e.g., field) rheometer and the known flour type using at least (i) the time-varying measurement of torque (e.g., minimum, maximum, and average torque curve data derived therefrom) for the calibration sample mixture and (ii) a torque data stream (e.g., minimum, maximum, and average torque curve data derived therefrom) generated by the non-calibration rheometer for a mixture comprising (a) a second portion of the calibration sample of flour of the known flour type (e.g., and known quantity) and (b) an amount of the liquid (e.g., water) based on the calibration amount of the liquid (e.g., equal to the calibration amount, or equal to an average of the calibration amounts used in the set of first calibration rheometers).

In certain embodiments, the adjustment model is determined using, or based on, a plurality of torque data streams generated using the set of first calibrating rheometers, wherein each of the mixtures of the known flour type for the set of first calibration rheometers comprises a calibration amount of the liquid (e.g., an amount determined to achieve a certain (e.g., peak) torque value).

In certain embodiments, the system is a member of a set of first calibration rheometers, wherein the time-varying measurement of torque for the calibration sample mixture is, itself, corrected using an adjustment model determined for the member of the set of first calibration rheometers using one or more torque data streams generated by one or more members of a set of second calibration rheometers (e.g., a second tier of calibration rheometers).

In another aspect, the disclosed methods and systems are directed to a method for generating a calibrated measurement of one or more properties (e.g., rheological properties, e.g., water absorption and/or mixing characteristics) of a sample mixture comprising (i) flour of a known flour type and known quantity and (ii) a determined amount (e.g., to achieve a certain (e.g., peak) torque value) of a liquid (e.g., water), the method comprising: introducing the known quantity of the known flour type and the determined amount of the liquid into a dough rheometer comprising a mixing container (e.g., a stainless steel bowl, or other enclosure), one or more mixing blades (e.g., a sigmoid z-arm mixing blade), and one or more torque sensors for generating a time-varying (e.g., continuous) measurement of sample torque (from which minimum, maximum, and average curve data is derived) encountered by one or more of the one or more mixing blades when mixing the sample mixture in the mixing container; adjusting, by a processor of a computing device, (e.g., in real-time, during data acquisition), the time-varying measurement of sample torque (e.g., by application of an adjustment model) using the torque curve data (e.g., the minimum, maximum, and average curve data) generated from a set of first calibration rheometers (e.g., a set of one or more, e.g., one, two, three, or more, rheometers) operating, respectively, on one or more calibration samples comprising the known flour type [e.g., and a calibration amount of the liquid (e.g., to achieve the certain torque value)]; and determining (e.g., and displaying a representation of), by the processor, the one or more properties (e.g., an adjusted torque curve e.g., for each of the minimum, maximum, and average curve), a calibrated rheological property value, and/or an indication of compliance or non-compliance with a product specification of the sample mixture from the adjusted time-varying measurement of sample torque.

The "determined amount" of the liquid introduced into the rheometer need not necessarily be determined prior to introduction into the mixture, nor must the "determined amount" be specifically quantified at any point in time in terms of mass of liquid added, but rather, the "determined amount" may reflect a precise adjustment of the amount of liquid added during the process of introduction into the rheometer to achieve a particular predetermined condition (e.g., an amount of liquid added to achieve a certain predetermined peak torque value measured by the rheometer for the sample mixture).

In certain embodiments, the adjusting step comprises adjusting, by the processor, the time-varying measurement of sample torque using an adjustment model, wherein the adjustment model is based on a comparison of: (i) torque curve data (e.g., derived minimum, maximum, and average curve data) generated from the set of first calibration rheometers, each first calibration rheometer operating on (a) a first portion of a calibration sample comprising the known flour type and (b) a calibration amount of the liquid (e.g., an amount of liquid to achieve the certain peak torque value); and (ii) torque curve data (from which minimum, maximum, and average curve data is derived) generated by the dough rheometer operating on a second portion of the calibration sample and an amount of the liquid that is based on the calibration amounts of liquid used in the set of first calibration rheometers (e.g., the exact same amount, e.g., an average amount, e.g., a median amount, e.g., a statistically relevant amount). During calibration, the first and second portions of the calibration sample are from the same batch, although once the adjustment model is derived, it can be applied to torque measurements (minimum, maximum, and average) from a sample mixture that comprises flour from a different batch (but of the same type).

In certain embodiments, the torque curve data (e.g., used to generate the adjustment model) reflects a calibration (e.g., has been previously calibrated) using one or more torque data streams generated from a set of second calibration rheometers (e.g., second tier calibration rheometers) for samples comprising the known flour type (e.g., wherein the set of second calibration rheometers is one or more laboratory dough rheometers, e.g., one or more industry-accepted third-party laboratory dough rheometers).

In certain embodiments, the adjusting step comprises adjusting, by the processor, the real-time measurement of (e.g., field-based) sample torque using an adjustment model specific to the known flour type (e.g., wherein said adjustment model is also device-specific).

In certain embodiments, the determined amount of liquid is that which achieves a predetermined (e.g., peak) torque value, wherein the predetermined (e.g., peak) torque value is the same as that for which amounts of water were adjusted in experiments performed with each rheometer of the set of first calibration rheometers to generate the torque curve data (e.g., the adjustment model).

Elements of embodiments described with respect to a given aspect of the invention may be used in various embodiments of another aspect of the invention. For example, it is contemplated that features of dependent claims depending from one independent claim can be used in apparatus, articles, systems, and/or methods of any of the other independent claims.

BRIEF DESCRIPTION OF THE DRAWINGS

The foregoing and other objects, aspects, features, and advantages of the present disclosure will become more apparent and better understood by referring to the following description taken in conjunction with the accompanying drawings, in which.

Figure 1:
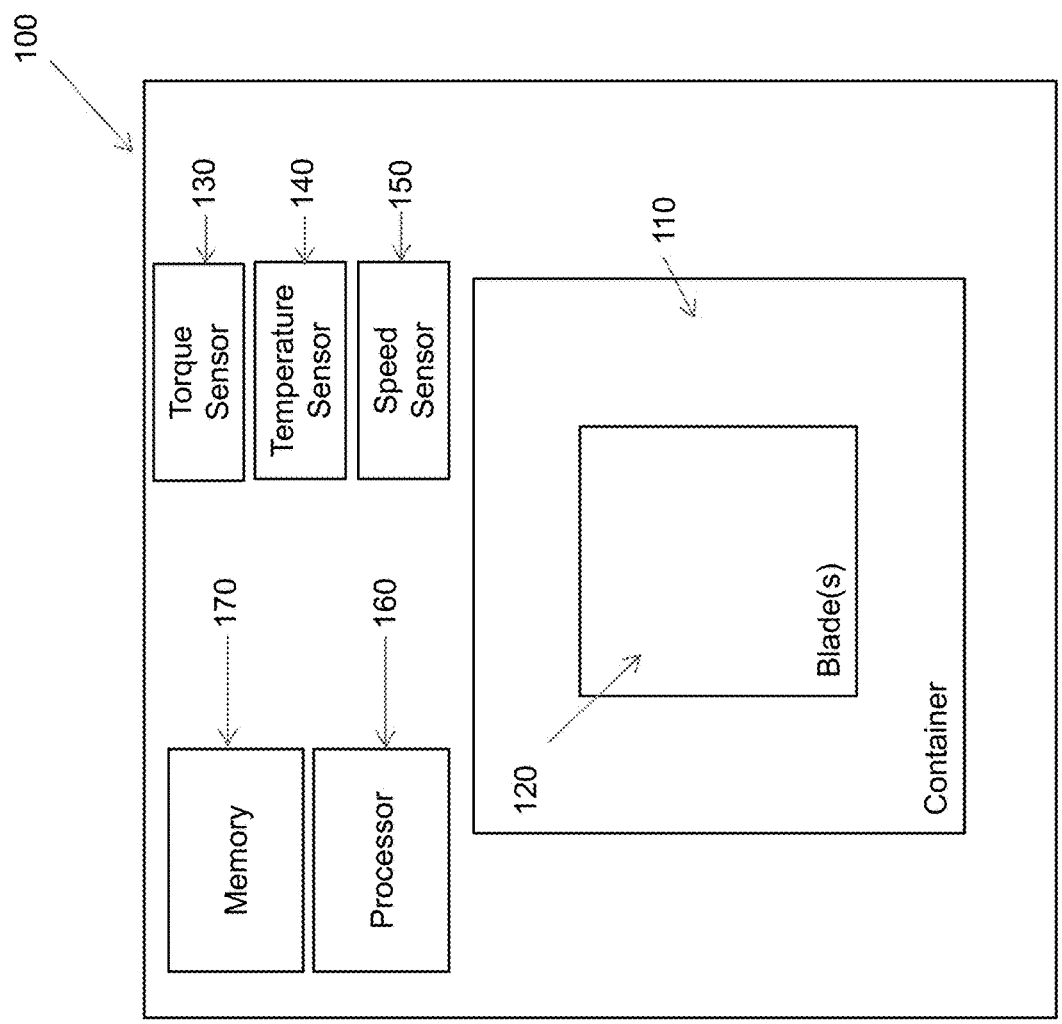
FIG. 1 is a schematic of a rheometer for obtaining a calibrated measurement of one or more properties of a sample mixture, according to an illustrative embodiment.

The features and advantages of the present disclosure will become more apparent from the detailed description set forth below when taken in conjunction with the drawings, in which like reference characters identify corresponding elements throughout. In the drawings, like reference numbers generally indicate identical, functionally similar, and/or structurally similar elements.

DETAILED DESCRIPTION

It is contemplated that systems, devices, methods, and processes of the claimed invention encompass variations and adaptations developed using information from the embodiments described herein. Adaptation and/or modification of the systems, devices, methods, and processes described herein may be performed by those of ordinary skill in the relevant art.

Throughout the description, where articles, devices, and systems are described as having, including, or comprising specific components, or where processes and methods are described as having, including, or comprising specific steps, it is contemplated that, additionally, there are articles, devices, and systems of the present invention that consist essentially of, or consist of, the recited components, and that there are processes and methods according to the present invention that consist essentially of, or consist of, the recited processing steps.

It should be understood that the order of steps or order for performing certain action is immaterial so long as the invention remains operable. Moreover, two or more steps or actions may be conducted simultaneously.

Headers are provided for the convenience of the reader and are not intended as limiting the scope of the material organized thereby.

The mention herein of any publication, for example, in the Background section, is not an admission that the publication serves as prior art with respect to any of the claims presented herein. The Background section is presented for purposes of clarity and is not meant as a description of prior art with respect to any claim.

As used herein, "real-time" means performed with a processor substantially at the same time relative to another event such that a user of the disclosed systems and methods discerns no time lapse between the real-time results and the non-processed results. For example, real-time adjustments to measurements means adjustments made to measurements by a processor upon receiving the measurements and presentation of the adjusted measurements to a user within a timeframe that the user would have expected the presentation of the non-adjusted results.

The present disclosure encompasses the recognition that each dough rheometer has its own unique, relatively consistent set of performance characteristics. In other words, when operating within specification, the internal repeatability of each dough rheometer makes the discrepancies predictable between devices measuring the same flour using substantially the same test conditions. Observations of the relationship between rheological measurements obtained from different dough rheometers have revealed that measurement discrepancies (e.g., of torque) vary not only between different rheometers, but the discrepancies themselves vary differently with time during a given test. For example, the ratio of torque readings from two dough rheometers may fluctuate over the course of a standard 20-minute test. For example, at time "6 minutes, 20 seconds" rheometer "A" might yield a torque reading 1.03 times the torque reading from rheometer "B", while at time "13 minutes, 37 seconds", the ratio might be 0.95.

The relationship between time-varying measurements from different dough rheometers has been found to be relatively consistent for a given type of flour. This relationship varies by flour type (e.g., based on the protein content of the flour). Examples of different flour types, for example, based on grades (e.g., B, S, G, H, WW), ash content (e.g., mineral content after milling of the flour), protein content, and wheat mix are shown in Table 1.

TABLE 1

Examples of different flour types.

| Grade - Straight Flour | Ash Content | Protein Content | Wheat Mix |
|---|---|---|---|
| B | 0.53% (±0.3%) | 11.5% (±0.5%) | 30% Spring Wheat 70% Winter Wheat |
| S | 0.53% (±0.3%) | 12.4% (±0.3%) | 75% Spring Wheat 25% Winter Wheat |
| G | 0.52% (±0.2%) | 13.2% (±0.5%) | 100% Spring Wheat |
| H | 0.55% (±0.3%) | 14.0% (±0.3%) | 100% Spring Wheat |
| WW | 1.70% (+/−0.30%) | 13.7% (+/−0.3%) | 100% Spring Wheat |

It has also been observed that the amplitude (bandwidth) of the torque measurements can vary within a test, between tests, between instruments of the same make, and between different makes of instruments, without noticeable variance in the average torque. The difference in torque bandwidths between two instruments may have only a small effect on the variance in their water absorption results, but a large effect on other quality parameters (e.g., dough stability) that are derived from the curvature of the torque curve. It is therefore important to account for the torque bandwidth as well as the torque average at each measurement point. As will be discussed herein, the torque bandwidth can be understood to be the difference between the derived minimum and maximum torque curves that are based on the "raw" torque data (with the raw torque data also being the basis for the average torque curve). As will be further discussed, each of the derived minimum, maximum, and average torque curves can be used in the alignment/adjustment model. As used herein, the terms "torque curve" and "torque spectra" are equivalent.

The measurement results obtained from different dough rheometers can be adjusted (e.g., calibrated), as described herein, in an instrument-specific and flour type-specific manner that accounts for the time-dependence and flour-type dependence of the time-varying torque measurements. In certain embodiments, the adjustment described herein is performed using adjustment models generated, in part, from industry-accepted data (e.g., from measurements obtained from third-party "reference" laboratories) as a calibration reference. The adjustment models may be generated, for example, using multiple linear regression, multivariate linear regression, nonlinear regression, or other techniques, using the time-dependent derived minimum, maximum and average torque curves as described herein. As used herein, an adjustment model may be expressed, for example, as one or more functions, one or more numerical parameters of one or more functions, or a combination of one or more functions and one or more numerical parameters thereof.

FIG. 1 is a schematic of a rheometer 100 for obtaining a calibrated measurement of one or more properties (e.g., rheological properties, e.g., water absorption and/or mixing characteristics) of a sample mixture. It is understood that the components of the FIG. 1 schematic are illustrative of different functional components and the arrangement is merely for illustrative purposes and shall not be limiting of any embodiment. For example, certain components of FIG. 1 may be rearranged, configured differently, and/or combined into a single component without any effect on the disclosed methods and systems.

Each rheometer 100 includes a mixing container 110, one or more mixing blades 120, at least one torque sensor 130, at least one temperature sensor 140, and at least one speed sensor 150. Mixing container 110 can be a stainless steel bowl or other enclosure. Mixing blade(s) 120 can be a sigmoid z-arm mixing blade. The sensors 130, 140 and 150 obtain and/or generate a time-varying measurement of sample torque (e.g., the rotational force) encountered by mixing blade(s) 110, mixing container temperature and relayed speed, respectively, when the sample mixture is mixed in mixing container 110. The sensors 130, 140 and 150 can obtain measurements continuously or discretely in a substantially continuous manner.

It shall be understood that methods and systems disclosed herein are performed under and/or are subject to sample conditions (e.g., sample moisture content) and test conditions (e.g., test temperature and mixing speed) that must be substantially the same or consistent between the sets of rheometers on which comparisons are to be made, and any substantial differences in sample conditions (e.g., moisture content) must be adjusted and/or accounted for prior to or during the measurement of the properties of interest. For example, the same temperature and mixing speed must be used, and there must be appropriate control of these test conditions within the tolerances specified by the respective instrument manufacturer. Additionally, moisture content of a sample must be checked at each test site, and any differences must be accounted for by adjusting sample conditions (e.g., sample and liquid amounts used) during analysis.

Referring back to FIG. 1, a rheometer 100 according to the disclosed methods and systems also includes a processor 160 and memory 170. When an alignment/adjustment model for the rheometer 100 has been created or generated according to the disclosed methods and systems, memory 170 stores instructions which, when executed by processor 160, cause processor 160 to adjust the time-varying minimum, maximum and average measurements of sample torque derived from the measurements obtained by torque sensor 130. The time-varying, temperature- and speed-dependent torque measurements are adjusted using a torque data stream (also comprising derived minimum, maximum, and average torque data curves) from a set of first rheometers as set forth in FIG. 2. As provided herein previously, for example, the time-varying measurements of sample torque may be adjusted using an adjustment model created from the torque data stream from the set of first rheometers. As used herein, a "set" may have one, two, three, four, five, or more members.

Figure 2:
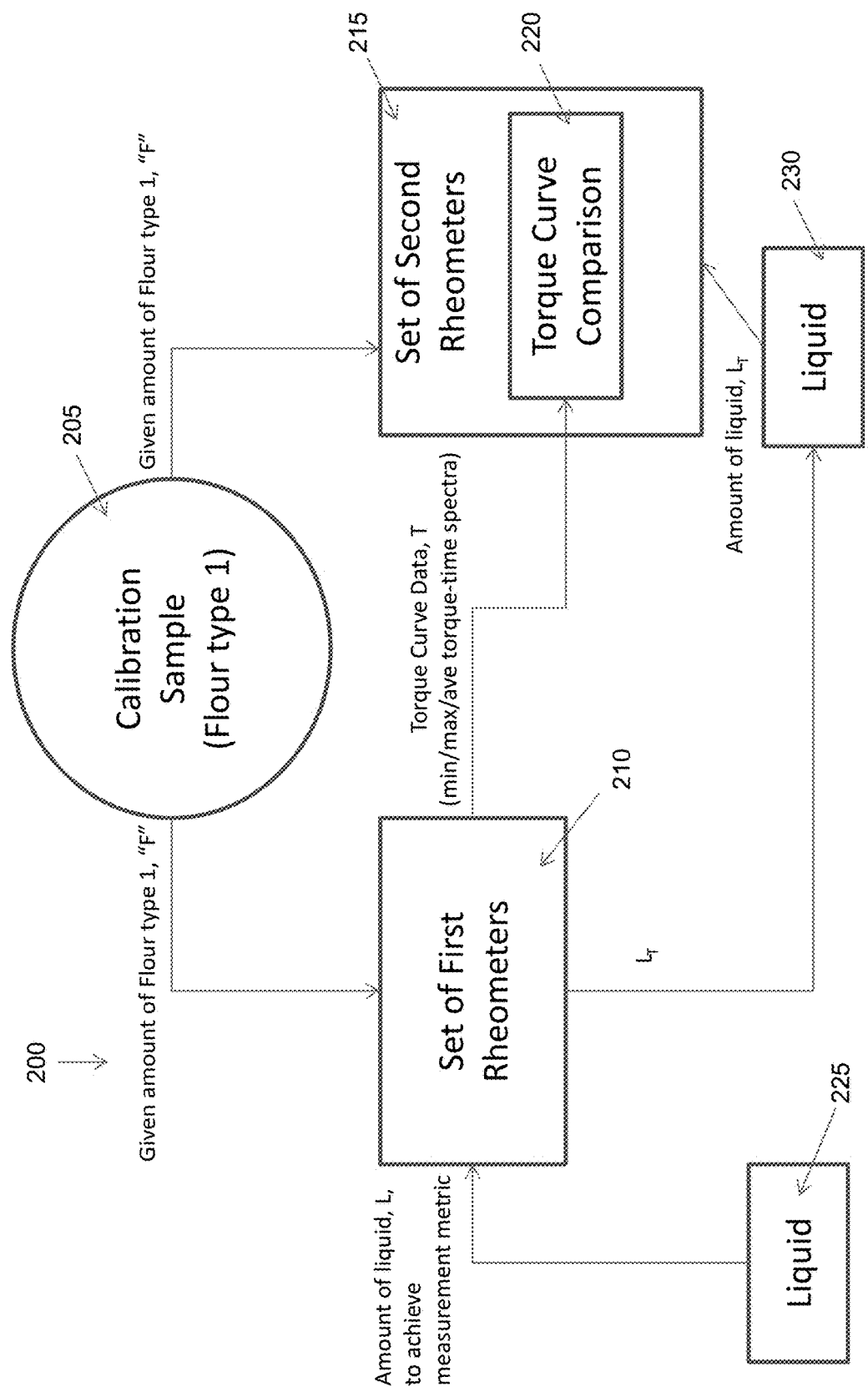
FIG. 2 is a schematic of a system for calibrating a second dough rheometer to a first dough rheometer, according to an illustrative embodiment.

FIG. 2 is an example of a part of the process described herein for generating an adjustment model. As shown in the block flow diagram 200 of FIG. 2, a calibration sample 205 from a particular flour type, shown as "Flour type 1" is used to supply a given quantity of flour sample, F, to each member of a set (e.g., one or more) of first rheometers 210 and a set (e.g., one or more) of second rheometers 215, e.g., where the moisture content of the flour sample is known and compensated for in the determination of quantity F. Additionally, for each of the first rheometers 210, an amount of liquid 225, L, corrected for the moisture content of the flour, is added to the flour to achieve a certain measurement metric. An example measurement metric could be a peak measurement of five hundred (500) Force Units of torque (1 Force Unit=9.806 mNm), e.g., where the peak measurement is achieved and the measured torque then gradually decreases over time as mixing continues. The amount of liquid that needs to be added to achieve this metric may vary slightly from rheometer to rheometer within the set of first rheometers, because, in addition to being a function of the water absorption capacity of the flour, L is also a function of the individual rheometer geometry, which may vary slightly from machine to machine. First rheometers 210 will each generate a series of torque measurements over time, referred to herein as "torque curve" or "torque curve data." As provided herein, the torque measurements for each rheometer (e.g., taken at a rate of 100 samples/second) are down-sampled (e.g., to a rate of 1 sample/second) to allow for the generation of three torque data curves: a minimum, maximum, and average torque curve (e.g., computing the minimum, maximum, and average for each 100 samples within each one-second window, and extrapolating between points), thereby allowing for a computation of the torque bandwidth (e.g., difference between maximum and minimum torque curves) for each point in time for the total duration of the torque measurement. The torque bandwidth can be further utilized in the development of the alignment model, and computation of rheological and/or dough properties. The derived torque curve data (e.g., three curves) from the first set rheometers can be combined (e.g., averaged) to generate a single composite representative "reference" torque curve that represents the minimum torque-time spectra, another composite "reference" torque curve that represents the maximum torque-time spectra, and a third composite "reference" torque curve that represents the average torque-time spectra, all three reference curves representative of the first set of rheometers. The composite/reference/curve data can be provided to each of a set of second rheometers 215. It can be understood that in the disclosed methods and systems, an "average" or other combination of data may allow for the identification and elimination of outlier data prior to combining, averaging, etc. For example, each of the first set rheometers may perform a test on one or more samples of the calibration flour sample as provided herein, each time/test generating three (minimum, maximum, and average) torque curves. When multiple calibration samples of the same flour type are tested by the same first set rheometer to generate multiple triplets of torque curves, the triplet of torque curves from the same first set rheometer can be combined (e.g., averaged, median, etc.) to generate a single combined triplet torque set for each first set rheometer. The combined triplet torque curves from each first set rheometer can then be further combined (e.g., averaged, median, etc.) to form a composite triplet torque curve set from the first set rheometers, T, as show in FIG. 2. In other embodiments, torque curve data can be combined (e.g., averaged) before the down-sampling or filtering that generates the triplet torque curves, whereby a single set of triplet torque curves can be obtained from the combined, raw torque data. In such embodiments, raw torque data can be combined from each test run by each first set rheometer on a given calibration sample, then the combined raw torque data from each first set rheometer further combined (e.g., average, median, etc.) to generate a composite single raw torque data set from which the triplet torque curve data can be derived for that rheometer. A composite triple torque curve data set, T, can be derived by combining the resulting triplets (curve-by-curve, e.g., by averaging the respective maximum, minimum, and average curves; taking the median of the respective maximum, minimum, and average curves, etc.). In yet another embodiment, all raw torque data measurements of the same calibration sample from all first set rheometers can be combined to form a composite raw torque data stream, from which a single composite torque curve triplet (minimum, maximum, average), T, can be derived. It can be understood that there are many ways to combine the data from multiple first set rheometers, and the disclosed methods and systems shall not be limited to the method by which the torque data from the first set rheometers is combined, nor the form of the data (e.g., raw torque data or derived torque curve triplet) when it is combined, nor the point at which the triplet curve data is obtained.

Each of the second set rheometers 215 will also receive a given amount of flour, F, of "Flour type 1" from the same calibration sample/batch of "Flour type 1" as that supplied to the first rheometers 210. Each of the second set rheometers 215 will also receive an amount of liquid, $L_T$, 230 that is based on or representative of L values, the amounts provided to the set of first rheometers 210 (e.g., $L_T$ may be an average of the first rheometer L amounts). In certain embodiments, this value $L_T$ is expressed as an absorption value, e.g., water absorption capacity, not to be confused with moisture content. Moisture content is known and, in certain embodiments, is the same for each of the flour samples, having been accounted for in the determination of flour sample quantity F used in each of the first set rheometers and second set rheometers. Amount $L_T$, 230, is fixed and is not altered to precisely achieve the aforementioned certain measurement metric (e.g., 500 Force Units of torque) as was done with each of the first rheometers 210. Rather, torque data at second set rheometers is measured using $L_T$, 230, such that a comparison between the torque curve data from the first set (average or reference torque curve data) and torque measurements at each second set rheometer can be performed, and an adjustment model obtained for each second set rheometer. As such, $L_T$, 230, and the torque curve data shall be communicated to each member of the second rheometer set 215 using known communication and/or data transfer techniques, and such data transfer can occur electronically or in another manner, and may be directly or indirectly transferred from the set of first rheometers 210 to each second set rheometer 215.

In an example embodiment where there is one first rheometer and one or more second rheometers, the amount of liquid (e.g., water), L, provided to first rheometer may be the same amount of liquid, $L_T$, communicated and then provided to all members of the set of second rheometers. Similarly, in that same embodiment, a single torque curve representing each of minimum, maximum, and average torque-time spectra from the first rheometer, can be transferred from the first rheometer to each of the members of the set of second rheometers.

In another example embodiment where there is more than one first rheometer and one or more second rheometers, each of the amounts of liquid provided to each member of the set of first rheometers can be represented as $L_1, L_2, \ldots, L_N$, where N is the number of first rheometers, and the amount of liquid, $L_T$, communicated to and provided to each member of the set of second rheometers can be a statistically relevant composite amount based on $L_1, L_2, \ldots, L_N$, for example, the average, the median, or another amount based on $L_1, L_2, \ldots L_N$. Similarly, a single set of torque curve data, T, representing the minimum, maximum and average torque-time spectra of the set of first rheometers, will be transferred from the set of first rheometers to each member of the set of second rheometers, where the transferred single torque curve data (for each of the three curves) is based on a statistically relevant composite amount based on the N torque data curves (for each of the three torque curves) generated by or derived from the N first set rheometers. For example, the transferred torque curve data, T, for each of the minimum, maximum, and average curves can be based on the average (e.g., at each point in time) of the various N first rheometer torque curve data measurements, respectively, for the minimum, maximum, and average torque curves generated at each of the N first set rheometers.

As shown in FIG. 2, the set of second rheometers 215 are in communication with a torque curve comparison module 220, each of which is capable of receiving the torque curve data transferred from the first set rheometers 210 and is able to compare the transferred torque curve data to torque curve data generated by or corresponding to measurements taken by each respective second set rheometer 215 using the given amount F of calibration sample 205 of Flour Type 1 and the amount of liquid $L_T$ as indicated by the first set rheometers 210. As provided herein, each second set rheometer will cause the generation of derived minimum, maximum, and average torque-time spectra. The adjustment model for each second set rheometer 215 (and that flour type) is obtained by comparing or aligning the "second" torque data curves generated using F and $L_T$ by each second set rheometer 215, using multivariate analysis (e.g. multiple linear regression), with the torque curve data, T, transferred/obtained from the first set rheometers 210. Each minimum, maximum and average torque-time spectrum derived from a second set rheometer is compared to the minimum, maximum and average torque-time spectrum of the first set rheometer, T, to create an adjustment model to adjust the torque curve data from the second set rheometer to that of the first set rheometer. In some embodiments, the entirety of the first set rheometer data, T (e.g., data from all three (minimum, maximum, and average) curves), is used to adjust the data from each of the three curves generated by a second set rheometer.

The adjustment model may be implemented on a computer program (e.g., doughLAB for Windows software) or other processor instruction within the processor 160 of the rheometer (e.g., doughLAB), via an adjustment module (e.g., Prediction Pack), providing real-time adjustment of torque. Thus, using the adjustment module, a second set rheometer can display, in real-time (as the test progresses), adjusted torque values for one or more of the minimum, maximum, and average torque curves that closely match a first set rheometer. The alignment thus occurs at each second set rheometer, with the alignment being between the respective second rheometer torque curve data, over time, with the transferred torque curve data, T, from the first rheometer set 210, thereby providing the basis for an adjustment model, for each of the rheometers in the second set 215. In this manner, by applying an applicable adjustment model to applicable second set rheometer data, each second set rheometer 215 can be calibrated with the first set rheometers 210. As provided herein, the adjustment model is specific to each second set rheometer 215, and is also specific to the particular flour type being measured. In certain embodiments, each second set rheometer has ten, five, four, three, two, or one adjustment model(s), each, for example, corresponding to the type of flour being measured, where each type may have a different protein content (e.g., flour of a type shown in Table 1).

It shall be understood that the aforementioned calibration must be performed for each flour type, and thus, for example, the process described herein in relation to FIG. 2 can be carried out with flour samples of each type of flour shown in Table 1 such that each second set rheometer contains a set of torque curve data adjustment models, one model for each flour type. It shall also be understood that the disclosed methods and systems are not limited to first and second sets of rheometers, and that a set of third rheometers could be similarly calibrated to the second set rheometers (and hence first set rheometers) by extending the use of the calibration flour sample to the set of third rheometers, generating and transferring composite torque curve data from the second rheometer set to the third set rheometers, and generating torque curve data at the third set rheometers using the same amount, $L_T$, of liquid. In yet another embodiment, once second set rheometers are calibrated to first set rheometers based on the process depicted in FIG. 2, third set rheometers can be calibrated to second set rheometers using the same process depicted in FIG. 2, with second set rheometers becoming the "first" set, and third set rheometers becoming the "second" set, as "first" and "second" are referred to in FIG. 2. It should be noted that in such scenario, the calibration flour may be from a completely different batch than used to calibrate the second set to the first set, and thus, the second set must apply its respective adjustment models in generating its torque curve data, prior to (e.g., averaging, etc.) transmission of the torque curve data to the third set rheometers. In this manner, third set rheometers can be aligned with first set rheometers by twice using the process depicted in FIG. 2. The disclosed methods and systems are not so limited to three sets or tiers of rheometers, and can be extended as needed.

It shall be understood with reference to FIG. 2 that the "torque curve comparison" may be a module resident on each second set rheometer or a module in communication with one or more second set rheometers.

The adjustment model may be determined for each second set rheometer using known comparative mathematical methods (e.g., regression models, multivariate regression models, linear regression models, multiple linear regression, multivariate linear regression models, curve fitting, Honigs' regression, nearest neighbor, etc.) to identify relationships (over time) between the torque-time spectra from the first set rheometers and torque-time spectra from the given/respective second set rheometer. As provided herein, some (e.g., the respective minimum, maximum, or average curve data) or all of the data, T, from the first set rheometers can be used to determine the alignment model for each of the three (minimum, maximum, and average) torque curves associated with each of the second set rheometers. As stated herein, an adjustment model is specific to the type of flour being measured and the second set rheometer being used for a measurement. Once obtained, the adjustment model can be applied in certain embodiments to torque measurement data in real-time, e.g., for a sample of the specific type of flour but from a batch other than the batch used to generate the adjustment model. It can be additionally understood that the methods and processes in FIG. 2 can be repeated at periodic intervals, given the nature of the different rheometers and changes thereto over time. As such, new adjustment models for each of the different flour types can be generated at specified intervals, e.g., every twelve weeks, once per quarter, every six months, or another period.

It can also be understood that variations of the methods and processes in accordance with FIG. 2 can occur. For example, in the simple embodiment of one first rheometer, the given amount of flour, F, can be further subdivided into two or more equal amounts, $f_j$, where j is the number of equal subdivisions of F. Torque curve data can thus be generated j different times by the first set rheometer (using same conditions), and then averaged to further account for variability amongst the single first rheometer. It can be understood that this division can occur with multiple first set rheometers, where each can provide an average torque curve data (for each of the minimum, maximum, and average curves) over j different measurements, each of which can be further averaged for provision of a single torque curve data set, T, to the second set rheometers.

Figure 3:
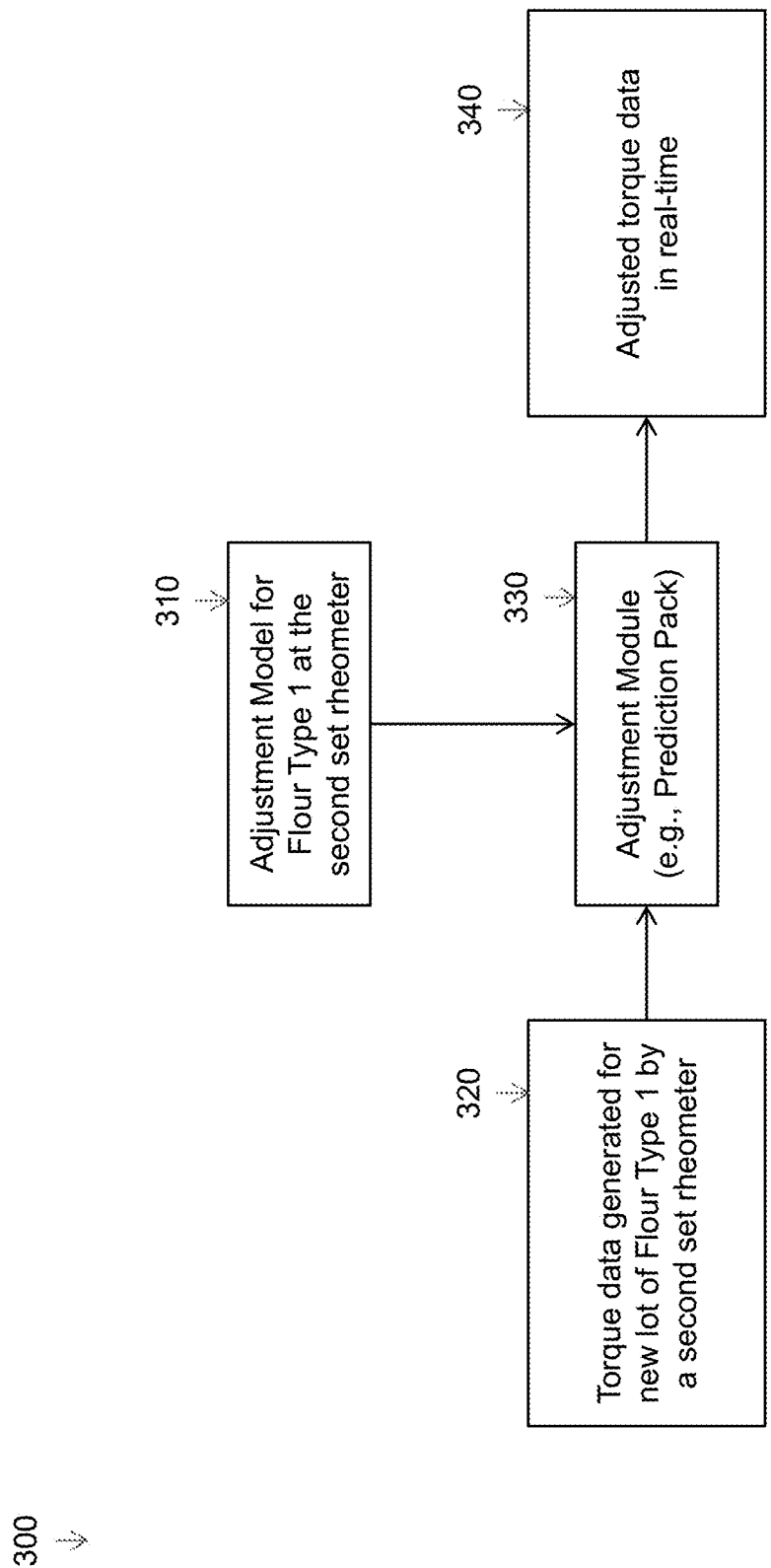
FIG. 3 is a block flow diagram depicting the adjustment of torque data from a dough rheometer using an adjustment module, according to an illustrative embodiment.

FIG. 3 shows an illustrative example, in the form of block flow diagram 300, of how torque data 310 obtained by second set rheometers can be adjusted using the appropriate adjustment model 320. As provided herein, adjustment model 320 is specific to a given flour type (e.g., a flour type shown in Table 1) and a particular second set rheometer. The adjustment model 320 is generated for the specific flour type and specific second set rheometer using methods and systems in accordance with FIG. 2.

As shown in FIG. 3, once calibrated to first set rheometers (e.g., adjustment models for respective flour types obtained using process of FIG. 2), second set rheometer can measure torque data, under controlled thermal and mechanical input (e.g., test temperature of 30.0° C. and mixing speed of 63 rpm on the slow blade of the mixing container), for a given flour type, e.g., "Flour Type 1", in accordance with typical practice (e.g., add appropriate liquid, e.g., water, to obtain particular measurement metric, e.g., 500 Force Units of torque), where such torque measurements over time can be provided to an adjustment module 330, which may, in real-time in some embodiments, be used to apply the respective adjustment model 320 for Flour Type 1 to the second set rheometer measured torque data 310 to generate adjusted torque data 340. Such adjustment can ensure the operator of the second set rheometer that the adjusted torque data 340 is adjusted to what the first set rheometer might measure if the first set rheometer were to measure Flour Type 1. When the set of first rheometers is a reference laboratory, for example, in this manner, it is hoped that there will be a reduction in the aforementioned instances of need for "arbitration" due to discrepancies between different non-reference rheometers that have been calibrated to the first set/reference rheometer (s). In certain embodiments, the adjustment module 340 may cause the adjusted torque data 330 to be displayed in real-time.

Returning to FIG. 1, memory 170 stores instructions which, when executed by processor 160, cause processor 160 to determine (e.g., and display a representation of) one or more properties of the sample mixture. For example, the properties may include an adjusted time-varying measurement of sample torque ("torque curve"), under controlled thermal and mechanical input, from which other properties, e.g., a calibrated rheological property value, are determined to indicate compliance or non-compliance with a product specification.

Figure 4:
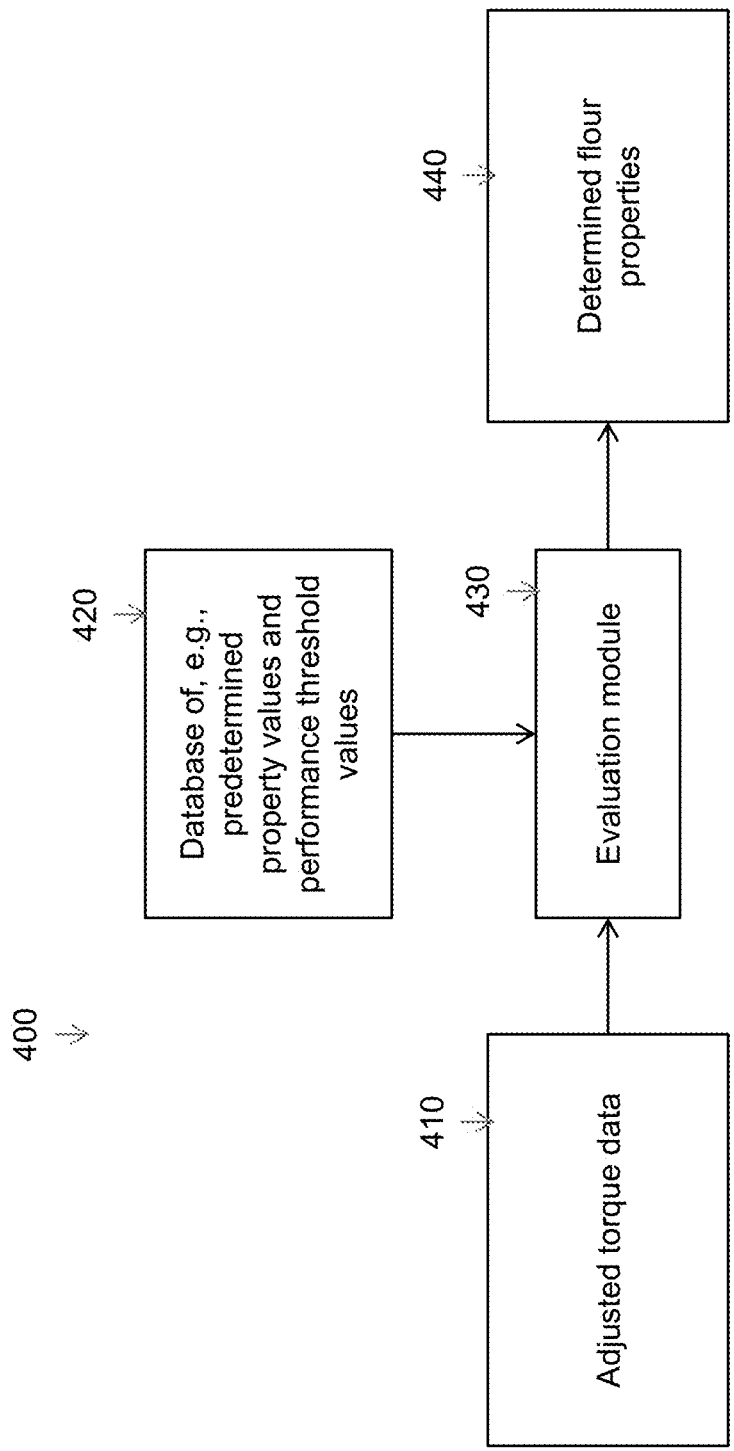
FIG. 4 is a block flow diagram depicting the determination of flour properties from adjusted torque data, according to an illustrative embodiment.

FIG. 4 is a block flow diagram 400 depicting the determination of flour properties 440 from an adjusted time-varying measurement of sample torque 410 using an evaluation module 430, according to an illustrative embodiment. The evaluation module can be based on a database 420 of predefined rules, property values (e.g., flour and/or dough properties), and/or other definitions. The determined flour properties can include an adjusted torque curve (minimum, maximum, and/or average) for the flour tested, a calibrated rheological property value for the flour and/or dough tested, and/or an indication of compliance or non-compliance with a product specification (e.g., to determine whether the flour is in-specification for a given use).

An adjusted torque curve (minimum, maximum, and/or average) can be obtained from the adjusted time-varying measurement of sample torque by, for example, displaying the adjusted torque curve data (minimum, maximum, and/or average) described above (e.g., in real-time, e.g., after the completion of a portion or all of a measurement). A calibrated rheological property value can be obtained from the adjusted time-varying measurement of sample torque, for example, from the adjusted torque curve data. As provided herein, in some instances, the bandwidth of the torque curve data (difference between maximum and minimum adjusted curve data) can be used to compute the calibrated rheological property value. An indication of compliance or non-compliance with a product specification can be obtained from the adjusted time-varying measurement of sample torque by comparing the adjusted torque curve data (or property data computed therefrom) to known torque data (or property data computed therefrom) stored in database 420 (e.g., to determine whether the flour is associated with a substantially similar torque curve to that of a known flour type or sample, e.g., within product specifications).

In certain embodiments, a set of rheometers may be rheometers deployed in the field (e.g., in a flour mill, e.g., at a food manufacturer) and another set of rheometers can be referred to as "master" rheometers (e.g., deployed in a dedicated laboratory) to which the field rheometers can be calibrated. For example, the master rheometers may be operated in a location that is remote from the field rheometers and the one or more master rheometers can be at different locations from each other (e.g., at different flour mills, e.g., different food manufacturers). The master set rheometers, in certain embodiments, include rheometers of the same size, type, and model. These master rheometers may have substantially the same mixing containers and mixing blades. For example, the master rheometers may be produced at approximately the same time, by the same staff, and/or at the same facility.

In certain embodiments, a further set of rheometers is used. For example, these are "reference" rheometers (e.g., industry-accepted third-party laboratory rheometers) that are used to calibrate the "master" rheometers. In some embodiments, the "reference" rheometers are of the same type or similar type as that of the first set and/or second set rheometers. In other embodiments, the "reference" rheometers include rheometers of a different type than that of the first and/or second set rheometers. In some embodiments, once reference rheometers are used to calibrate "master" rheometers (using methods and systems according to FIG. 2), the master rheometers can be used to calibrate the field rheometers (also in accordance with FIG. 2).

Figure 5A:
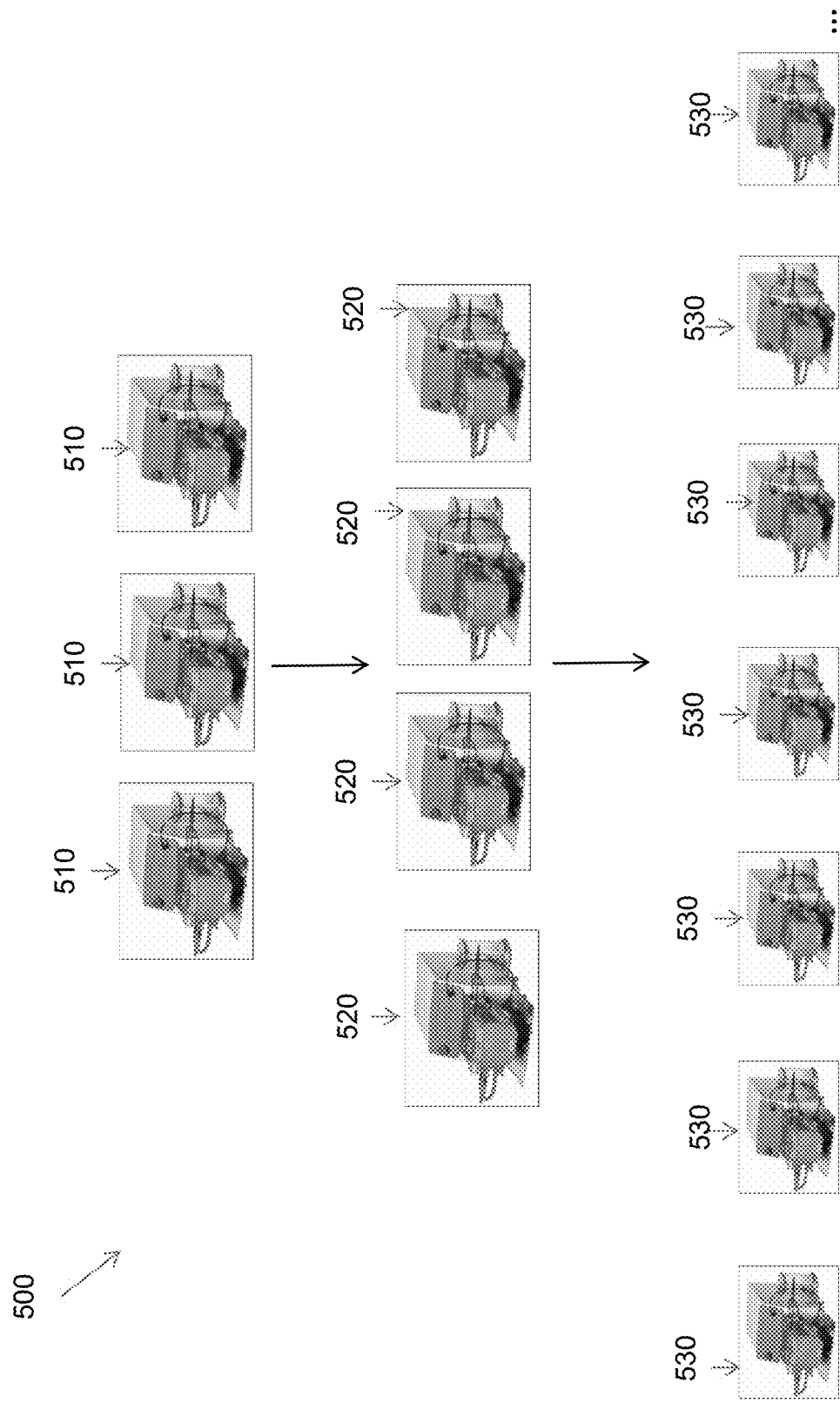
FIG. 5A is an illustration of two-tiered calibration of a plurality of rheometers (e.g., a plurality of field-deployed dough rheometers), according to an illustrative embodiment.

FIG. 5A provides one illustration of such a two-tiered calibration of a plurality of rheometers, in accordance with certain embodiments described herein. As depicted in diagram 500, in certain embodiments, a set of reference rheometers 510 is used to calibrate a set of master rheometers 520. Each of the set of master rheometers 520 is calibrated (e.g., aligned) using representative results (e.g., average torque curve data) determined from the reference rheometers 510 (e.g., operated at one or more third-party laboratories). The field rheometers 530 may be, for example, deployed at various mills, food manufacturers, and/or laboratories, and have adjustment models created by aligning their torque curve data to torque curve data generated by the master rheometers 520, which are, themselves, calibrated using torque curve data from the reference rheometers 510. In certain embodiments, there are at least two or at least three reference rheometers 510. In certain embodiments, there are at least three, at least four, or at least five master rheometers 520 (e.g., the set used to calibrate the set of field rheometers 530). In certain embodiments, there are more field rheometers than either master or reference rheometers. These rheometers transmit and receive information as explained in detail below.

Experimental Example: Two-Tiered Calibration of Torque Data

Figure 5B:
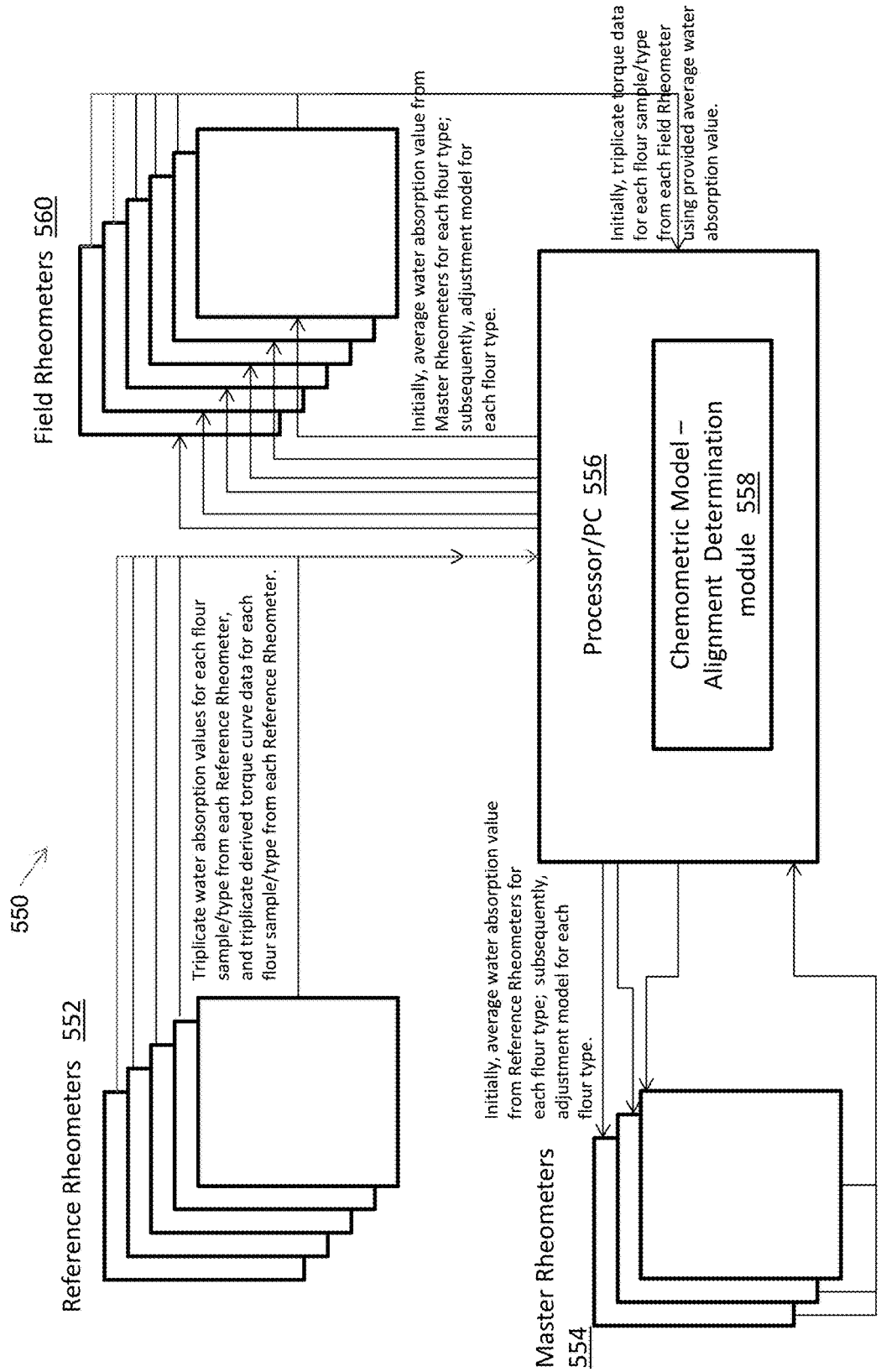
FIG. 5B is an illustration according to an example embodiment of the disclosed methods and systems.

As illustrated by the diagram 550 of FIG. 5B, flour samples were distributed to five (5) third-party "reference" laboratories 552 in various locations, and to three (3) master rheometers (the master group) 554. The reference laboratory samples of a given flour type were provided as a blind sample (e.g., flour type not identified to the reference laboratory) and each reference laboratory was asked to perform triplicate analyses of the given flour sample. The master group also received samples from the same flour batch (for each flour type) and was also asked to perform triplicate analyses on each sample using substantially the same test conditions; however, the samples sent to the master group were not blind (e.g., the master group ultimately knew the identity of each flour sample). In this manner, the master group, knowing the identity of the flour type, could ultimately classify an applicable adjustment model for each flour type/sample. (This procedure was repeated and/or performed for each flour type/sample.)

In this embodiment, the moisture values of the flour samples were determined by the flour source (e.g., miller) that generated the flour samples, and the moisture values were provided to the reference laboratories/rheometers and the master group rheometers with the respective flour samples. With this moisture information, each reference and master rheometer was able to use the same amount of dry solids for each triplicate analysis, e.g., the typical industry standard of 300.00 grams of flour, corrected to a 14% moisture basis; or otherwise stated, the same weight of dry solid as 300.00 grams of a flour sample at 14% moisture. For example, for flour at 13% moisture, the amount of flour used would be 296.55 grams; for flour at 11% moisture, 289.89 grams; and, for flour at 15% moisture, 303.53 grams, etc. It can be understood that the disclosed methods and systems are not limited to the flour amount used, and that other amounts and/or methods may be used for ensuring that substantially the same amount of dry solids is used in each experiment.

The reference laboratory rheometers were used to experimentally determine optimal water absorption values (e.g., amount of liquid/water added) for each flour sample to achieve a peak of 500 Force Units (1 Force Unit=9.806 mNm), using industry standard methods. The absorption values measured for each flour sample varied (e.g., within a set of triplicates of a single flour type) because of the blind nature of the tests and the inherent variability of the instruments/rheometers. The water absorption values determined from the rheometers at the five (5) reference laboratories were averaged (e.g., outliers eliminated prior to averaging) for each sample within the sets of triplicates, yielding a single absorption measurement for a given flour sample. In certain embodiments, the triplicate water absorption values from each reference rheometer were averaged, and the resulting five (5) average values were then averaged to generate the single average or expected water absorption value for (initial) transmission to each of the master rheometers. As shown in FIG. 5B, in this embodiment, this averaging was performed by a processor/computer 556 in communication with each of the reference laboratories, although the methods and systems are not limited to this configuration and it is possible, for example, for the processor instructions to be distributed at various processors and/or various locations.

Additionally, derived torque curve data, T (with reference to FIG. 2), consisting of minimum, maximum and average torque-time spectra, was generated for each of the triplicate samples (for a given flour type/sample) across the five different reference laboratory rheometers 552. For each respective flour sample/type, the derived torque curve data streams from the reference laboratory rheometers were averaged (e.g., outliers eliminated prior to averaging) (e.g., at the computer/processor 556) to yield one set of combined torque curve data, T, comprising minimum, maximum and average torque-time spectra, for each flour sample/type. As with the water absorption values, the fifteen sets of derived torque curve data, T, could be averaged (over time), or the three torque data measurements from each reference rheometer could be averaged, with the five resulting average torque curve data measurements for each of the minimum, maximum, and average further averaged to provide a single average torque curve data measurement, T, for each of the minimum, maximum and average torque-time spectra measured by the reference rheometers, for that flour type/sample. As shown in the FIG. 5B embodiment, this averaging of torque curve data was also performed by the processor/computer 556. (It is understood that the disclosed methods and systems are not limited to these combinatorial techniques; for example, in other embodiments, the raw/measured torque data from each rheometer could be averaged before being down-sampled to obtain the derived minimum, maximum, and average torque curve data for each reference rheometer, wherein such derived torque curve data T from each reference rheometer could then be averaged; or, in the example embodiment with five reference rheometers measuring three samples of each flour type, the raw/measured torque data from all fifteen measurements could be averaged and a single minimum, maximum, and average torque curve set, T, derived from the averaged raw/measured data. As provided herein, other manners of utilizing and/or combining the reference data (water absorption and/or torque) can be used without departing from the scope of the disclosed methods and systems.)

The average or expected water absorption values (and in embodiments where the master rheometers have processors with instructions to form the alignment module, the average torque curve data) were then transmitted (e.g., by the processor/computer 556) to the master rheometers 554. In the example embodiment, the expected/average water absorption value can be immediately transmitted to the master rheometers 554 (e.g., separately and ahead of any transmission of torque curve data in embodiments where such transmission occurs). In this manner, the master rheometers 554 are able to begin running their analysis of the same flour sample/type to allow for little time delay between analysis by the reference labs and the master rheometers. As shown in the FIG. 5B illustrative embodiment, this transmission of information was performed via and with the assistance of the processor/computer 556.

The amount of water added to each sample analyzed by the master rheometers 554 for the given flour type/sample was the same as the average amount as determined by the reference laboratory rheometers that produced a peak of 500 Force Units in the reference laboratory rheometers 552. The amount of flour used at the master rheometers was again set at the industry standard of the amount of dry solids equivalent to 300.00 grams of flour at 14% moisture, taking into account the moisture values provided by the source/miller. In the example embodiment, although the flour type of each sample was known at the master rheometer site, the actual operators of the master rheometers were not informed of the flour type, thereby making the rheometer operators "blind" to each sample type to avoid any operator bias in measurement at the master rheometers.

In the FIG. 5 embodiment, triplicate torque curve data (e.g., for each of the three samples, each derived torque curve data of minimum, maximum, and average) for each flour type/sample from each master rheometer was averaged (e.g., by the processor/computer 556, after being transmitted thereto) to provide a derived torque curve data set for each master rheometer. As provided previously herein, the disclosed methods and systems are not limited to averaging or combining the master rheometer data in any particular manner. For each master rheometer, the averaged torque curve data, including minimum, maximum and average torque-time spectra, for a given flour type/sample as measured by such master rheometer was aligned to the corresponding minimum, maximum and average torque-time spectra provided by the reference laboratories using a software program of a chemometric alignment module 558 that used multiple linear regression to model the relationship between the torque curve data streams. As provided previously herein, in the FIG. 5B embodiment, each of the minimum, maximum and average torque-time spectra provided by the reference laboratories was used to separately correct, adjust, or align each of the minimum, maximum and average torque-time spectra for a given flour type/sample as measured/derived by each master rheometer, and in this way, the bandwidth of the reference rheometers could be used in correcting or aligning the master rheometer data. The methods and systems are not limited to such alignment technique, and in other embodiments, e.g., only the "minimum" torque curve from the reference labs may be used to correct/align only the "minimum" torque curve data from a master rheometer, only the "maximum" torque curve data from the reference labs may be used to correct/align only the "maximum" torque curve data from a master rheometer, etc.

It should be understood that other mathematical treatments can be used together with or instead of multiple linear regression (e.g., multivariate linear regression, partial least squares, nearest neighbor, Honigs' regression, etc.). Based on this relationship of torque curve data, each master rheometer generated an adjustment model for the given flour type associated with the sample. As shown in FIG. 5B, the alignment and generation of adjustment models were performed by the processor/computer 556, and then the adjustment model for each master rheometer and each flour type was transmitted to each respective master rheometer to be applied whenever that same flour/sample type was tested in the future.

In subsequent analysis of a flour type at a master rheometer, the corresponding adjustment model for that flour type is applied, via implementation in the computer program 170, to the torque data obtained by each master rheometer to adjust the data to that of the average reference laboratory rheometers. This adjusted data was determined and displayed in real-time. This approach involved a dedicated test configuration for each flour type and for each master rheometer and resulted in adjusted torque data that represented the average results of the reference laboratories for that flour type.

To align the dough rheometers in the field, triplicate (non-blind) samples for each flour type were distributed to the set of master rheometers 554 and to rheometers in the field 560. Just as in the reference-to-master alignment process described herein, experiments were performed in triplicate at each of the master rheometers to produce triplicate torque data streams for each flour sample/type, with the amount of water added (e.g., water absorption) in each experiment precisely determined to produce a peak of 500 Force Units; however, it should be understood that the master rheometers 554 analyzed the samples while applying the applicable adjustment models (e.g., based on the reference laboratory torque data generated by the reference rheometers 552) for each respective flour type/sample, to identify the water absorption to achieve the desired peak torque metric of 500 Force Units. Each master rheometer thus generated a result using the same amount of dry solids (e.g., amount of dry solids equivalent to 300.00 grams of flour at 14% moisture) for a given flour product, consistent with the reference rheometers. As before, the triplicate torque data from the master rheometers 554 was averaged within each flour type/sample across all master rheometers. Once again, in this example embodiment which is depicted in FIG. 5B, the averaging was performed by the processor/computer 556 which was also in communication with each of the field rheometers 560. As provided herein, averaging is one method of combining the data, which in itself could be performed in a variety of ways, and all of such combinatorial techniques are envisioned to be within the scope of the disclosed methods and systems.

Just as in the laboratory-master calibration, in accordance with FIG. 2, the expected/average water absorption values for each flour sample that was obtained by the master rheometers 554, and with flour moisture values provided by the source/miller, were transmitted to the rheometers in the field 560 (although it can be understood that the transmission of moisture and average absorption values could be at different times, from different sources, and using different modes of communication/transmission). In the FIG. 5B embodiment, the processor/computer 556 communicated the average master rheometer water absorption value to each of the field rheometers 560. In the example embodiment, each rheometer in the field also performed triplicate analyses of each flour sample with the same amount of dry solids (e.g., amount of dry solids equivalent to 300.00 grams of flour at 14% moisture) as that used by the master rheometers, and the same amount of water added to each mixture, the amount of water being the average amount added for the corresponding flour product by the master rheometers for the same sample. This allowed for a direct comparison (in the FIG. 5B embodiment, by the processor 556) with the data from the master rheometers.

In the example embodiment, the field rheometers 560 conveyed their respective derived torque curve measurements, T, to the processor/computer 556 that was also in communication with the master rheometers 554. In the FIG. 5B embodiment, the processor/computer 556, equipped with the alignment determination module 558 (and the average torque curve data from the master rheometers), was capable of generating an adjustment model for a particular field rheometer and flour type by aligning the (average) torque curve data, T, for a given field rheometer and flour sample/type, with the average torque curve data generated by the master rheometers for that same flour sample/type. In the FIG. 5B embodiment, the adjustment model was also generated using multiple linear regression by using all three of the derived torque curves from the master rheometers to individually correct, align, or adjust each of the three derived torque curves from each of the field rheometers, although as provided herein, the disclosed methods and systems are not limited to this technique. In this embodiment, the processor/computer 556 could then communicate the adjustment model for a given flour type to a respective field rheometer, which would thereafter be able to apply the appropriate model in real-time to future measurements of that flour type by that field rheometer, including measurements of samples of that flour type from different batches than that used for generating the corresponding adjustment model. In this manner, each field rheometer was thus aligned to the combined result of the master rheometer group for each flour product, as described previously, which in-turn represented the average result of the third-party reference laboratories.

Figure 8A:
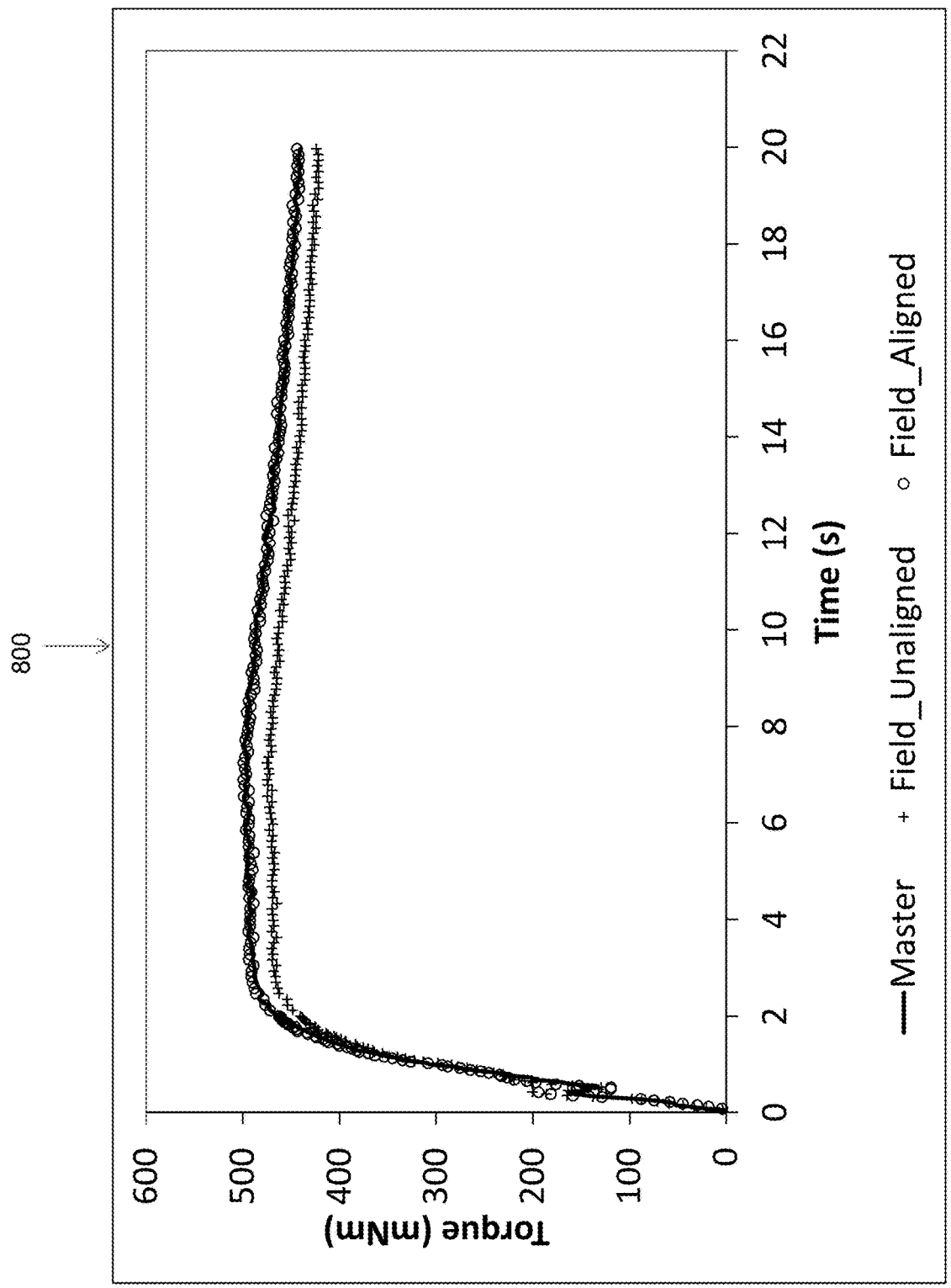
FIG. 8A is a plot of derived average torque curves for a field and master rheometers, according to an illustrative embodiment, while also showing the improvement in the torque alignment of a field rheometer to a master rheometer after the derived average torque curve is adjusted based on an appropriately determined (e.g., by flour/sample type) adjustment model for a system according to FIG. 5B.
Figure 8B:
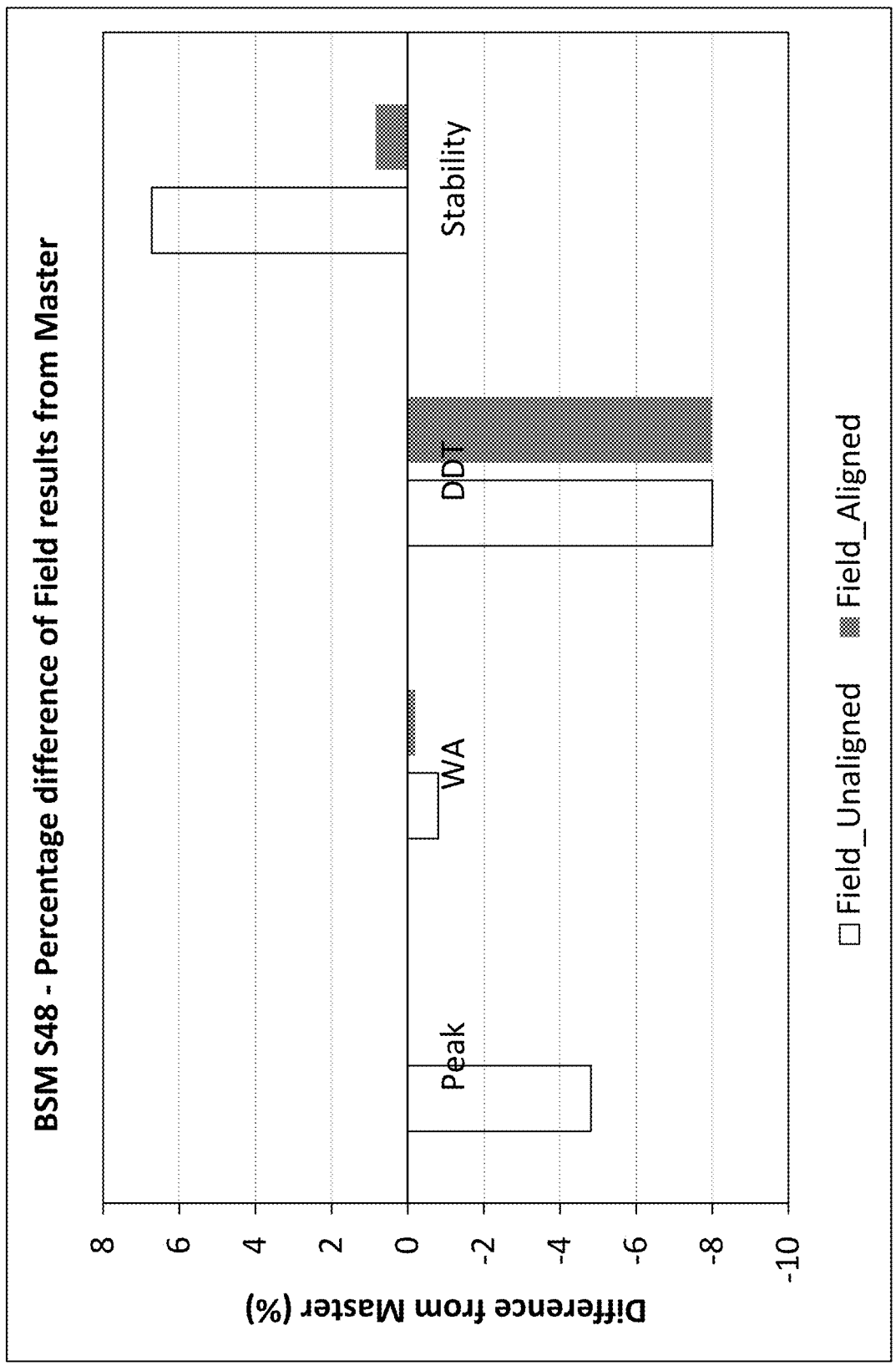
FIG. 8B shows the measurement of error of a field rheometer (before and after implementation of the torque adjustment model) to a master rheometer for a system according to FIG. 5B.

As a result of this approach, all of the rheometers in the field provided consistent results within the inherent repeatability constraints of the test itself. For a given flour type, the instrument-to-instrument variability across a fleet of devices was thus largely eliminated. FIG. 8A shows a comparison of the "average" (as opposed to maximum or minimum) derived torque curve data 800 from field rheometers before and after alignment following the approach described herein, against the "average" torque curve data from the reference/master. The percentage error of adjusted and unadjusted results from the field rheometer compared to those of the master is shown in FIG. 8B.

Illustrative Computer Network

Figure 6:
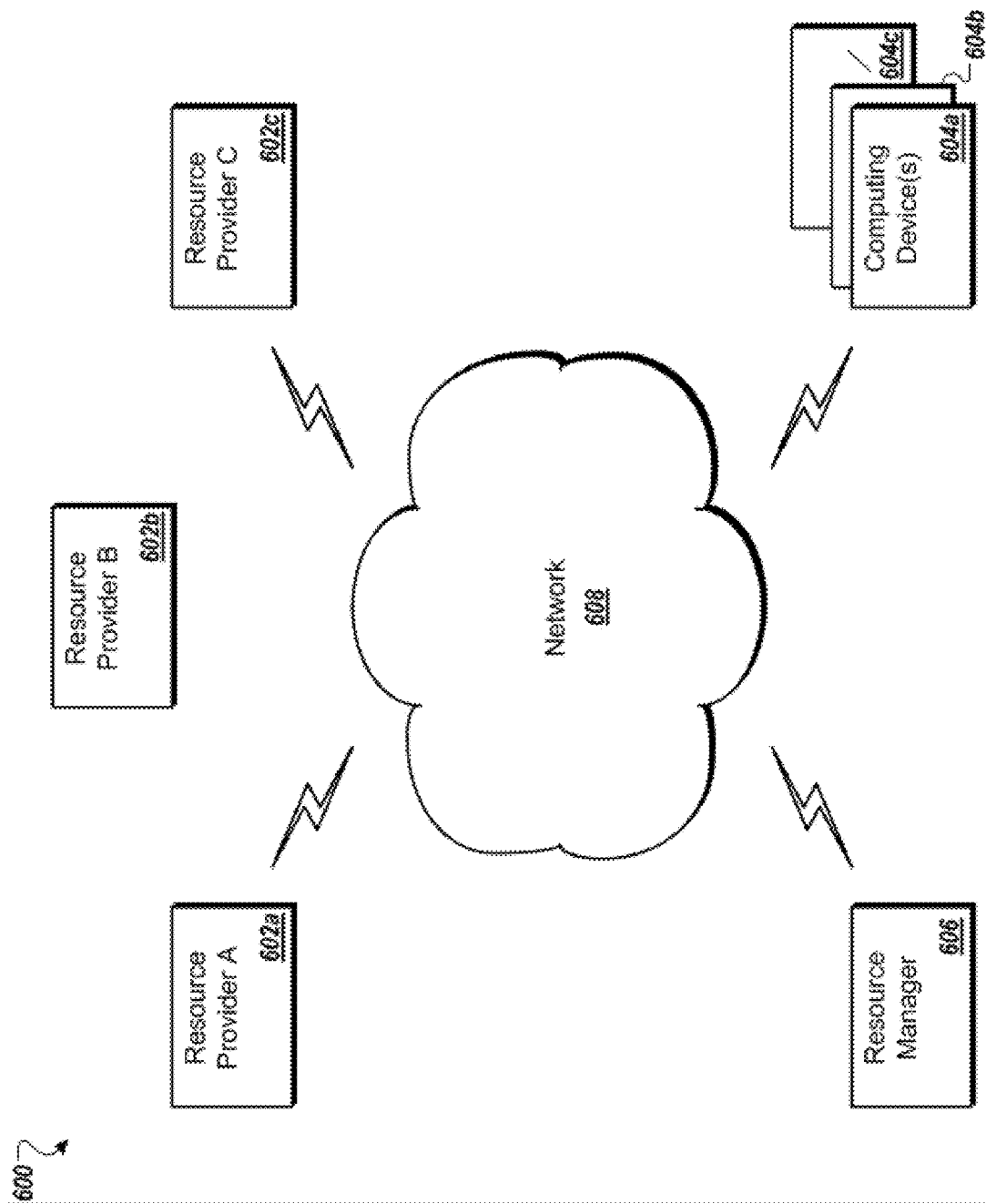
FIG. 6 is a block diagram of an example network environment for use in the methods and systems described herein, according to an illustrative embodiment.

As shown in FIG. 6, an implementation of a network environment 600 for use in the systems, methods, and architectures described herein, is shown and described. In brief overview, referring now to FIG. 6, a block diagram of an exemplary cloud computing environment 600 is shown and described. The cloud computing environment 600 may include one or more resource providers 602*a*, 602*b*, 602*c* (collectively, 602). Each resource provider 602 may include computing resources. In some implementations, computing resources may include any hardware and/or software used to process data. For example, computing resources may include hardware and/or software capable of executing algorithms, computer programs, and/or computer applications. In some implementations, exemplary computing resources may include application servers and/or databases with storage and retrieval capabilities. Each resource provider 602 may be connected to any other resource provider 602 in the cloud computing environment 600. In some implementations, the resource providers 602 may be connected over a computer network 608. Each resource provider 602 may be connected to one or more computing device 604*a*, 604*b*, 604*c* (collectively, 604), over the computer network 608.

The cloud computing environment 600 may include a resource manager 606. The resource manager 606 may be connected to the resource providers 602 and the computing devices 604 over the computer network 608. In some implementations, the resource manager 606 may facilitate the provision of computing resources by one or more resource providers 602 to one or more computing devices 604. The resource manager 606 may receive a request for a computing resource from a particular computing device 604. The resource manager 606 may identify one or more resource providers 602 capable of providing the computing resource requested by the computing device 604. The resource manager 606 may select a resource provider 602 to provide the computing resource. The resource manager 606 may facilitate a connection between the resource provider 602 and a particular computing device 604. In some implementations, the resource manager 606 may establish a connection between a particular resource provider 602 and a particular computing device 604. In some implementations, the resource manager 606 may redirect a particular computing device 604 to a particular resource provider 602 with the requested computing resource.

Figure 7:
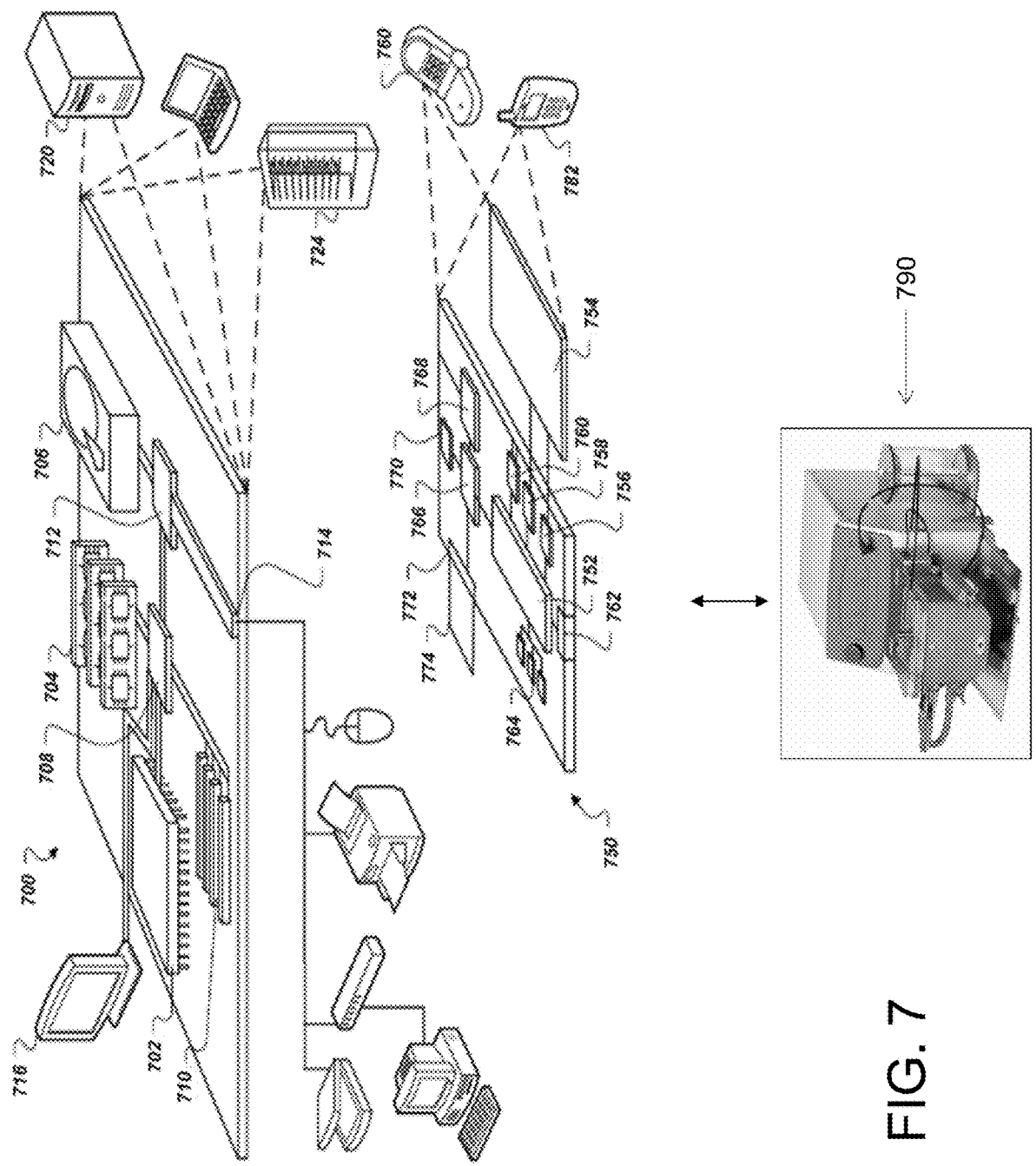
FIG. 7 is a block diagram of an example computing device and an example mobile computing device, for use in illustrative embodiments of the systems and methods described herein.

FIG. 7 shows an example of a computing device 700 and a mobile computing device 750 that can be operatively connected with rheometers 790 in the methods and systems described herein. Rheometers 790 can include first set rheometers, second set rheometers, and third set rheometers as described above. For example, in certain embodiments, rheometers 790 can include rheometers deployed in the field (e.g., rheometers 530 of FIG. 5A), master rheometers (e.g., rheometers 520 of FIG. 5A), and third-party laboratory rheometers (e.g., rheometers 510 of FIG. 5A). The computing device 700 is intended to represent various forms of digital computers, such as laptops, desktops, workstations, personal digital assistants, servers, blade servers, mainframes, and other appropriate computers. The mobile computing device 750 is intended to represent various forms of mobile devices, such as personal digital assistants, cellular telephones, smart-phones, and other similar computing devices. The components shown here, their connections and relationships, and their functions, are meant to be examples only, and are not meant to be limiting.

The computing device 700 includes a processor 702, a memory 704, a storage device 706, a high-speed interface 708 connecting to the memory 704 and multiple high-speed expansion ports 710, and a low-speed interface 712 connecting to a low-speed expansion port 714 and the storage device 706. Each of the processor 702, the memory 704, the storage device 706, the high-speed interface 708, the high-speed expansion ports 710, and the low-speed interface 712, are interconnected using various buses, and may be mounted on a common motherboard or in other manners as appropriate. The processor 702 can process instructions for execution within the computing device 700, including instructions stored in the memory 704 or on the storage device 706 to display graphical information for a GUI on an external input/output device, such as a display 716 coupled to the high-speed interface 708. In other implementations, multiple processors and/or multiple buses may be used, as appropriate, along with multiple memories and types of memory. Also, multiple computing devices may be connected, with each device providing portions of the necessary operations (e.g., as a server bank, a group of blade servers, or a multi-processor system). Thus, as the term is used herein, where a plurality of functions are described as being performed by "a processor", this encompasses embodiments wherein the plurality of functions are performed by any number of processors (one or more) of any number of computing devices (one or more). Furthermore, where a function is described as being performed by "a processor", this encompasses embodiments wherein the function is performed by any number of processors (one or more) of any number of computing devices (one or more) (e.g., in a distributed computing system).

The memory 704 stores information within the computing device 700. In some implementations, the memory 704 is a volatile memory unit or units. In some implementations, the memory 704 is a non-volatile memory unit or units. The memory 704 may also be another form of computer-readable medium, such as a magnetic or optical disk.

The storage device 706 is capable of providing mass storage for the computing device 700. In some implementations, the storage device 706 may be or contain a computer-readable medium, such as a floppy disk device, a hard disk device, an optical disk device, or a tape device, a flash memory or other similar solid state memory device, or an array of devices, including devices in a storage area network or other configurations. Instructions can be stored in an information carrier. The instructions, when executed by one or more processing devices (for example, processor 702), perform one or more methods, such as those described above. The instructions can also be stored by one or more storage devices such as computer- or machine-readable mediums (for example, the memory 704, the storage device 706, or memory on the processor 702).

The high-speed interface 708 manages bandwidth-intensive operations for the computing device 700, while the low-speed interface 712 manages lower bandwidth-intensive operations. Such allocation of functions is an example only. In some implementations, the high-speed interface 708 is coupled to the memory 704, the display 716 (e.g., through a graphics processor or accelerator), and to the high-speed expansion ports 710, which may accept various expansion cards (not shown). In the implementation, the low-speed interface 712 is coupled to the storage device 706 and the low-speed expansion port 714. The low-speed expansion port 714, which may include various communication ports (e.g., USB, Bluetooth®, Ethernet, wireless Ethernet) may be coupled to one or more input/output devices, such as a keyboard, a pointing device, a scanner, or a networking device such as a switch or router, e.g., through a network adapter.

The computing device 700 may be implemented in a number of different forms, as shown in the figure. For example, it may be implemented as a standard server 720, or multiple times in a group of such servers. In addition, it may be implemented in a personal computer such as a laptop computer. It may also be implemented as part of a rack server system 724. Alternatively, components from the computing device 700 may be combined with other components in a mobile device (not shown), such as a mobile computing device 750. Each of such devices may contain one or more of the computing device 700 and the mobile computing device 750, and an entire system may be made up of multiple computing devices communicating with each other.

The mobile computing device 750 includes a processor 752, a memory 764, an input/output device such as a display 754, a communication interface 766, and a transceiver 768, among other components. The mobile computing device 750 may also be provided with a storage device, such as a micro-drive or other device, to provide additional storage. Each of the processor 752, the memory 764, the display 754, the communication interface 766, and the transceiver 768, are interconnected using various buses, and several of the components may be mounted on a common motherboard or in other manners as appropriate.

The processor 752 can execute instructions within the mobile computing device 750, including instructions stored in the memory 764. The processor 752 may be implemented as a chipset of chips that include separate and multiple analog and digital processors. The processor 752 may provide, for example, for coordination of the other components of the mobile computing device 750, such as control of user interfaces, applications run by the mobile computing device 750, and wireless communication by the mobile computing device 750.

The processor 752 may communicate with a user through a control interface 758 and a display interface 756 coupled to the display 754. The display 754 may be, for example, a TFT (Thin-Film-Transistor Liquid Crystal Display) display or an OLED (Organic Light Emitting Diode) display, or other appropriate display technology. The display interface 756 may comprise appropriate circuitry for driving the display 754 to present graphical and other information to a user. The control interface 758 may receive commands from a user and convert them for submission to the processor 752. In addition, an external interface 762 may provide communication with the processor 752, so as to enable near area communication of the mobile computing device 750 with other devices. The external interface 762 may provide, for example, for wired communication in some implementations, or for wireless communication in other implementations, and multiple interfaces may also be used.

The memory 764 stores information within the mobile computing device 750. The memory 764 can be implemented as one or more of a computer-readable medium or media, a volatile memory unit or units, or a non-volatile memory unit or units. An expansion memory 774 may also be provided and connected to the mobile computing device 750 through an expansion interface 772, which may include, for example, a SIMM (Single In Line Memory Module) card interface or a DIMM (Double In Line Memory Module) card interface. The expansion memory 774 may provide extra storage space for the mobile computing device 750, or may also store applications or other information for the mobile computing device 750. Specifically, the expansion memory 774 may include instructions to carry out or supplement the processes described above, and may include secure information also. Thus, for example, the expansion memory 774 may be provided as a security module for the mobile computing device 750, and may be programmed with instructions that permit secure use of the mobile computing device 750. In addition, secure applications may be provided via the DIMM cards, along with additional information, such as placing identifying information on the DIMM card in a non-hackable manner.

The memory may include, for example, flash memory and/or NVRAM (non-volatile random access memory), as discussed below. In some implementations, instructions are stored in an information carrier and, when executed by one or more processing devices (for example, processor 752), perform one or more methods, such as those described above. The instructions can also be stored by one or more storage devices, such as one or more computer- or machine-readable mediums (for example, the memory 764, the expansion memory 774, or memory on the processor 752). In some implementations, the instructions can be received in a propagated signal, for example, over the transceiver 768 or the external interface 762.

The mobile computing device 750 may communicate wirelessly through the communication interface 766, which may include digital signal processing circuitry where necessary. The communication interface 766 may provide for communications under various modes or protocols, such as GSM voice calls (Global System for Mobile communications), SMS (Short Message Service), EMS (Enhanced Messaging Service), or MIMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication may occur, for example, through the transceiver 768 using a radio-frequency. In addition, short-range communication may occur, such as using a Bluetooth®, Wi-Fi™, or other such transceiver (not shown). In addition, a GPS (Global Positioning System) receiver module 770 may provide additional navigation- and location-related wireless data to the mobile computing device 750, which may be used as appropriate by applications running on the mobile computing device 750.

The mobile computing device 750 may also communicate audibly using an audio codec 760, which may receive spoken information from a user and convert it to usable digital information. The audio codec 760 may likewise generate audible sound for a user, such as through a speaker, e.g., in a handset of the mobile computing device 750. Such sound may include sound from voice telephone calls, may include recorded sound (e.g., voice messages, music files, etc.) and may also include sound generated by applications operating on the mobile computing device 750.

The mobile computing device 750 may be implemented in a number of different forms, as shown in the figure. For example, it may be implemented as a cellular telephone. It may also be implemented as part of a smart-phone 782, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

In some implementations, the modules (e.g. data aggregation module, mapping module, specifications module) described herein can be separated, combined or incorporated into single or combined modules. The modules depicted in the figures are not intended to limit the systems described herein to the software architectures shown therein.

Elements of different implementations described herein may be combined to form other implementations not specifically set forth above. Elements may be left out of the processes, computer programs, databases, etc. described herein without adversely affecting their operation. In addition, the logic flows depicted in the figures do not require the particular order shown, or sequential order, to achieve desirable results. Various separate elements may be combined into one or more individual elements to perform the functions described herein.

While the disclosed methods and systems have been particularly shown and described with reference to specific preferred embodiments, it should be understood by those skilled in the art that various changes in form and detail may be made therein without departing from the spirit and scope of the invention as defined by the appended claims.

What is claimed is:

1. A system for generating a calibrated measurement of one or more properties of a sample mixture, the sample mixture comprising (i) flour of a known flour type at known moisture; and (ii) a controlled amount of liquid adjusted to the known moisture of the sample mixture, the system comprising:
- a) at least one first and at least one second measuring device, each measuring device comprising:
  - I. a mixing container;
  - II. at least one mixing blade; and
  - III. at least one torque sensor for generating a time-varying measurement of sample torque encountered by one or more of the at least one mixing blade when mixing the sample mixture in the mixing container;
- b) a processor; and
- c) a memory having instructions stored thereon, wherein the instructions, when executed by the processor, cause the processor to:
  - I. adjust the generated time-varying measurement of sample torque of the at least one second measuring device to obtain an adjusted time-varying measurement of sample torque, based on a comparison of:
    - (i) at least one time-varying measurement of sample torque determined by the at least one first measuring device operating, respectively, on a first portion of a calibration sample comprising the known flour type and a calibration amount of the liquid, and,
    - (ii) at least one time-varying measurement of sample torque determined by the respective second measuring device operating on a second portion of the calibration sample and an amount of the liquid that is based on the calibration amount of the liquid; and,
  - II. determine the one or more properties of the sample mixture based on the adjusted time-varying measurement of sample torque.

2. The system of claim 1, wherein the instructions, when executed by the processor, cause the processor to adjust the generated time-varying measurement of sample torque of the at least one second measuring device using an adjustment model based on the comparison of (i) and (ii).

3. The system of claim 1, wherein the sample mixture comprises flour of the same type as the calibration sample, but from a different batch than the calibration sample.

4. The system of claim 1, where the system is a dough rheometer, and the one or more properties include rheological properties that include at least one of water absorption and mixing characteristics.

5. The system of claim 1, wherein the at least one time-varying measurement of sample torque determined by the at least one first measuring device and the at least one second measuring device, comprises three derived torque curves, where the three derived curves include a down-sampled, time-varying data derived from the at least one torque sensor that measures the time-varying sample torque, the down-sampled time-varying representations including a minimum time-varying torque spectrum, a maximum time-varying torque spectrum, and an average time-varying torque spectrum.

6. The system of claim 5, wherein the instructions to adjust the generated time-varying measurement of sample torque of the at least one second measuring device, include instructions to generate an adjustment model by comparing (i) at least one of the derived minimum, maximum, and average down-sampled time-varying spectra of sample torque determined by the at least one first measuring device operating, respectively, on a first portion of a calibration sample comprising the known flour type and a calibration amount of the liquid, with (ii) at least one of the derived minimum, maximum, and average down-sampled time-varying spectra of sample torque determined by the at least one second measuring device operating, respectively, on the second portion of the calibration sample comprising the known flour type and the calibration amount of the liquid.

7. The system of claim 6, wherein the adjustment model further comprises instructions to adjust one or more of the derived minimum, maximum, and average down-sampled time-varying spectra associated with the second measuring device with data from each of the minimum, maximum, and average down-sampled time-varying spectra of sample torque associated with the first measuring device.

8. A system according to claim 1, wherein the at least one time-varying measurement of sample torque determined by the at least one first measuring device operating, respectively, on a first portion of a calibration sample comprising the known flour type and a calibration amount of the liquid, comprises; at least two different measurements of torque determined by each of the at least one first measuring device operating on the calibration sample, wherein the at least two different measurements are combined.

9. A system according to claim 8, wherein the at least two different measurements from each first measurement device are combined by averaging.

10. A system according to claim 8, wherein the at least two different measurements from each first measurement device are combined to provide a combined result from each first measurement device, and the combined result from each first measurement device is further combined to generate a composite result from all of first measurement devices.

11. A system according to claim 1, wherein each measuring device further comprises at least one temperature sensor for controlling a the thermal input to the sample mixture, and at least one speed sensor for providing a measurement of the at least one mixing blade.

12. A system according to claim 1, where the comparison is based on at least one of: a regression, a multivariate regression, a linear regression, a multiple linear regression, a multivariate linear regression, a curve fitting, a Honigs' regression, a linear least squares, a Gaussian, and a nearest neighbor determination.

13. A dough rheometer for generating a calibrated measurement of one or more properties of a sample mixture comprising (i) flour of a known flour type at known moisture, and known quantity and (ii) a determined amount of a liquid adjusted to the known moisture of the sample mixture, the dough rheometer comprising:
- a) a mixing container;
- b) one or more mixing blades;
- c) one or more torque sensors for generating a time-varying measurement of sample torque encountered by one or more of the one or more mixing blades when mixing the sample mixture in the mixing container;
- d) a processor; and
- e) a memory having instructions stored thereon, wherein the instructions, when executed by the processor, cause the processor to:
  - I. adjust, in real-time, the time-varying measurement of sample torque using torque curve data generated from a set of first calibration rheometers operating, respectively, on one or more calibration samples comprising the known flour type; and adjust the generated time-varying measurement of sample torque using an adjustment model, wherein the adjustment model is based on a comparison of:
    - a) torque curve data generated from the set of first calibration rheometers, each first calibration rheometer operating on (i) at least one first portion of a calibration sample comprising the known flour type at known moisture and (ii) calibration amount of the liquid, adjusted to the known moisture of the sample mixture; and b) torque curve data generated by a set of second calibration rheometers operating on a second portion of the calibration sample and an amount of the liquid that is based on the calibration amounts of liquid used in the set of first calibration rheometers; and II. determine the one or more properties of the sample mixture from the adjusted time-varying measurement of sample torque.

14. The dough rheometer of claim 13, wherein the torque curve data generated from the set of second calibration rheometers reflects a calibration using one or more torque curves generated from a set of first calibration rheometers for calibration samples comprising the known flour type.

15. The dough rheometer of claim 14 wherein the instructions, when executed by the processor, cause the processor to adjust the time-varying measurement of sample torque to the torque curve data using an adjustment model specific to the known flour type at known moisture.

16. The dough rheometer of claim 13, wherein each of the one or more calibration samples operated on by the set of first calibration rheometers comprises a calibration amount of the liquid, adjusted to known moisture of the sample mixture.

17. A system for generating a torque curve adjustment model for use in a dough mixture comprising a known flour type at known moisture, the system comprising:
a) a mixing container;
b) one or more mixing blades;
c) one or more torque sensors for generating a time-varying measurement of sample torque encountered by one or more of the one or more mixing blades when mixing a calibration sample mixture comprising (i) a first portion of a calibration sample of flour of the known flour type and moisture, and known quantity and (ii) a determined calibration amount of a liquid, adjusted to the known moisture of the dough mixture, in the mixing container;
d) a processor; and
e) a memory having instructions stored thereon, wherein the instructions, when executed by the processor, cause the processor to:
I. generate a time-varying measurement of torque for the calibration sample mixture; and
II. determine the torque curve adjustment model for a non-calibration rheometer and the known flour type at known moisture using at least (i) the time-varying measurement of torque for the calibration sample mixture and (ii) a torque data stream generated by the non-calibration rheometer for a mixture comprising (a) a second portion of the calibration sample of flour of the known flour type and moisture and (b) an amount of the liquid based on the calibration amount of the liquid, adjusted to the known moisture of the dough mixture.

18. The system of claim 17, wherein the torque curve adjustment model is determined using a plurality of torque data streams generated using a set of first calibrating rheometers, and wherein each of the mixtures of the known flour type and moisture for the set of first calibration rheometers comprises a calibration amount of the liquid.

19. The system of claim 17, wherein the system is a member of a set of first calibration rheometers, and wherein the time-varying measurement of torque for the calibration sample mixture is, itself, corrected using an adjustment model determined for the member of the set of first calibration rheometers using one or more torque data streams generated by one or more members of a set of reference calibration rheometers.

* * * * *